(12) United States Patent
Mukherjee et al.

(10) Patent No.: US 11,119,158 B2
(45) Date of Patent: Sep. 14, 2021

(54) WIRELESS MECHANISM FOR DETECTING AN OPEN OR CLOSED CONTAINER, AND METHODS OF MAKING AND USING THE SAME

(71) Applicant: Thin Film Electronics ASA, Oslo (NO)

(72) Inventors: Somnath Mukherjee, Milpitas, CA (US); James Godfrey, Hertfordshire (GB)

(73) Assignees: Thin Film Electronics ASA, Oslo (NO); GlaxoSmithKline Intellectual Property Development Limited, Middlesex (GB)

( * ) Notice: Subject to any disclaimer, the term of this patent is extended or adjusted under 35 U.S.C. 154(b) by 0 days.

(21) Appl. No.: 16/309,673

(22) PCT Filed: Jun. 19, 2017

(86) PCT No.: PCT/IB2017/000872
§ 371 (c)(1),
(2) Date: Dec. 13, 2018

(87) PCT Pub. No.: WO2017/216632
PCT Pub. Date: Dec. 21, 2017

(65) Prior Publication Data
US 2019/0132658 A1 May 2, 2019

Related U.S. Application Data

(60) Provisional application No. 62/351,875, filed on Jun. 17, 2016.

(51) Int. Cl.
*G01R 31/50* (2020.01)
*G01D 5/20* (2006.01)
(Continued)

(52) U.S. Cl.
CPC ......... *G01R 31/50* (2020.01); *A61M 15/0026* (2014.02); *B65D 79/02* (2013.01);
(Continued)

(58) Field of Classification Search
None
See application file for complete search history.

(56) References Cited

U.S. PATENT DOCUMENTS 3,827,291 A * 8/1974 McCalvey ............... G01B 7/24
73/779
6,107,920 A 8/2000 Eberhardt et al.
(Continued)

FOREIGN PATENT DOCUMENTS

GB 2461099 A1 12/2009
WO 2006102678 A1 9/2006
(Continued)

OTHER PUBLICATIONS

International Preliminary Report on Patentability dated Dec. 27, 2018; International Application No. PCT/IB2017/000909; 7 pages; The International Bureau of WIPO, Geneva, Switzerland.
(Continued)

*Primary Examiner* — Thomas S McCormack
(74) *Attorney, Agent, or Firm* — James P. Riek

(57) ABSTRACT

An electronic device including a continuity sensor and electrical circuitry configured to detect and report the continuity state of an article, container or product packaging is disclosed. The continuity sensor includes a first substrate with first and second coils thereon, and a second substrate with a third coil thereon. The first coil has an integrated circuit electrically connected thereto. The first substrate is part of, or is attached or secured to a part of the article, container or packaging. The second substrate is another part of, or is attached or secured to another part of the article,
(Continued)

container or packaging. One of the article, container or packaging parts is (re)movable with respect to the other part. The first and second coils have one coupling when the article, container or packaging is closed or sealed, and a different coupling when the article, container or packaging is open or unsealed.

37 Claims, 15 Drawing Sheets

(51) Int. Cl.
| | |
|---|---|
| G08B 13/12 | (2006.01) |
| G08B 13/24 | (2006.01) |
| G06K 19/07 | (2006.01) |
| B65D 79/02 | (2006.01) |
| G01N 27/02 | (2006.01) |
| A61M 15/00 | (2006.01) |
| H04B 5/00 | (2006.01) |
| H04Q 9/00 | (2006.01) |

(52) U.S. Cl.
CPC ............ *G01D 5/204* (2013.01); *G01D 5/206* (2013.01); *G01D 5/2053* (2013.01); *G01D 5/2066* (2013.01); *G01D 5/2073* (2013.01); *G01N 27/025* (2013.01); *G06K 19/0716* (2013.01); *G06K 19/0717* (2013.01); *G08B 13/126* (2013.01); *G08B 13/2431* (2013.01); *H04B 5/0031* (2013.01); *H04Q 9/00* (2013.01); *A61M 15/00* (2013.01); *A61M 2202/064* (2013.01); *A61M 2205/14* (2013.01); *A61M 2205/3317* (2013.01); *H04Q 2209/40* (2013.01)

(56) References Cited

U.S. PATENT DOCUMENTS

| | | | |
|---|---|---|---|
| 8,534,281 B2 | 9/2013 | Davies et al. | |
| 8,746,242 B2 | 6/2014 | Connell et al. | |
| 10,371,737 B2 | 8/2019 | Mukherjee | |
| 2004/0007554 A1 | 1/2004 | Ribi | |
| 2006/0214789 A1 | 9/2006 | Posamentier et al. | |
| 2007/0069895 A1 | 3/2007 | Koh | |
| 2009/0109032 A1 | 4/2009 | Braun et al. | |
| 2009/0184085 A1 | 7/2009 | Ribi | |
| 2011/0210093 A1 | 9/2011 | Ribi | |
| 2015/0091502 A1 | 4/2015 | Mukherjee et al. | |
| 2015/0097443 A1 | 4/2015 | Moyer et al. | |
| 2015/0100335 A1 | 4/2015 | Englehard et al. | |
| 2016/0051776 A1 | 2/2016 | Von Hollen | |
| 2017/0290527 A1 | 10/2017 | Morrison et al. | |
| 2017/0328761 A1* | 11/2017 | Schwartz | G01F 23/266 |

FOREIGN PATENT DOCUMENTS

| | | |
|---|---|---|
| WO | 2014147550 A1 | 9/2014 |
| WO | 20140147550 A1 | 9/2014 |
| WO | WO 2016/007357 | 1/2016 |
| WO | 2016/033421 A1 | 3/2016 |
| WO | 20160033421 A1 | 3/2016 |
| WO | 2017/216632 A1 | 12/2017 |
| WO | 2017/216634 A3 | 12/2017 |
| WO | 2017/221242 A1 | 12/2017 |
| WO | 2017221242 A1 | 12/2017 |

OTHER PUBLICATIONS

International Search Report and Written Opinion; International Search Authority/EP dated Dec. 8, 2017; International Application No. PCT/IB2017/000909; 8 pgs; International Searching Authority/European Patent Office; NL.

International Search Report and Written Opinion; International Searching Authority/EP dated Dec. 1, 2017; International Searching Authority/EP dated Dec. 1, 2017; International Application No. PCT/IB2017/000872; 10 pgs.; International Searching Authority/European Patent Office; NL.

\* cited by examiner

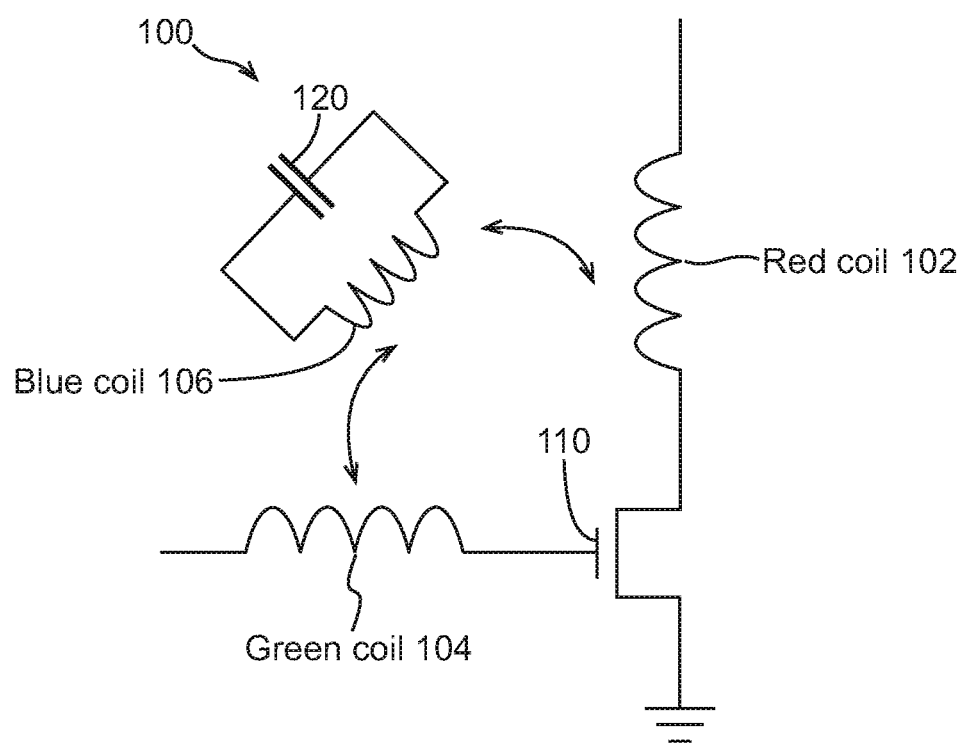

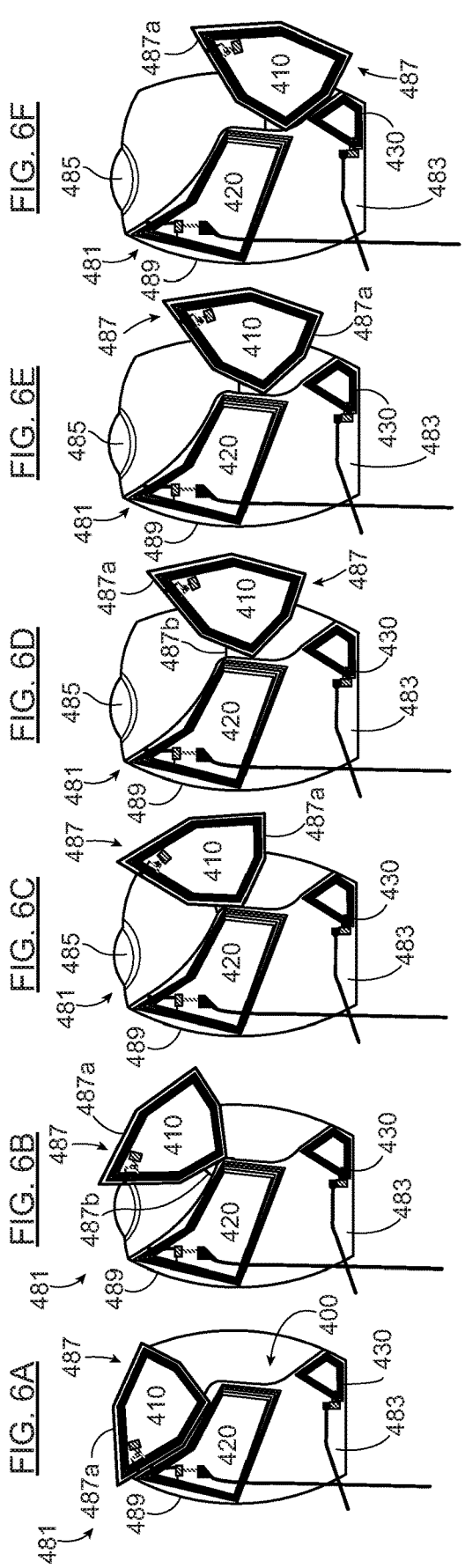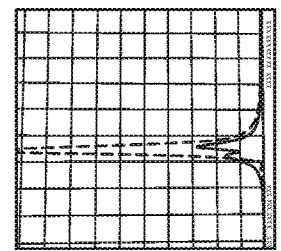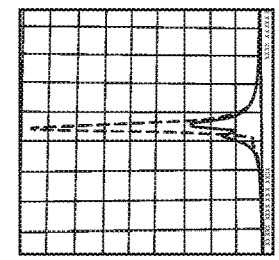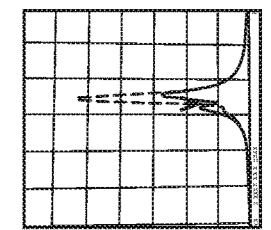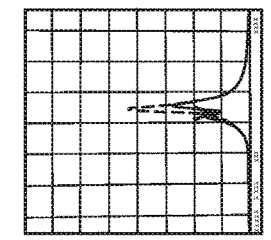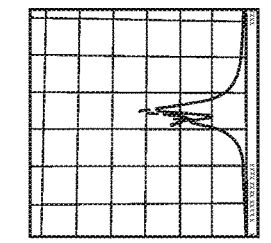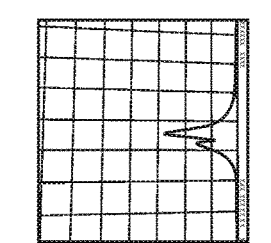

WIRELESS MECHANISM FOR DETECTING AN OPEN OR CLOSED CONTAINER, AND METHODS OF MAKING AND USING THE SAME

RELATED APPLICATIONS

This application is filed pursuant to 35 U.S.C. § 371 as a United States National Phase Application of International Patent Application Serial No. PCT/IB2017/000872 filed 19 Jun. 2017, which claims priority to U.S. Application No. 62/351,875 filed 17 Jun. 2016, and the entire contents of each of the foregoing applications are hereby incorporated by reference.

FIELD OF THE INVENTION

The present invention generally relates to (i) product security and authenticity and/or (ii) sensing or monitoring the state and/or use of an article. More specifically, embodiments of the present invention pertain to an electronic device/coil system/sensor and methods of making and using the same, in which the electronic device/coil system/sensor includes a plurality of coils for detecting an open or closed article container or product packaging. The present invention may also relate to a device and method for repeatedly detecting one of multiple states or modes of an article such as a container, housing or packaging for a product. For example, the device and method can determine the state of an article having a part (such as a lid or a cap) that is repeatedly movable between first and second states (e.g., corresponding to the article being open or closed).

DISCUSSION OF THE BACKGROUND

Certain product security and authentication technology relies on a wire that is torn or twisted off when the product packaging is opened. Ensuring a reliable, complete and irreversible tear can be challenging in various situations. Moreover, such technology can sense an opening event only once.

It can be useful to detect different positions of a part of an article that can move repeatedly between the different states. For example, certain medicine dispensers, such as blister packs and other multi-compartment pill or tablet dispensers, pumps, inhalation devices, etc., can be opened and closed (or raised and lowered) to obtain or deliver a dose of medication. Detection of the different positions (which can correspond to different states or modes) of such medicine dispensers is useful for monitoring a patient's compliance and/or adherence with a medicinal therapy or regimen.

In more detail, there are instances where it is useful to detect which state a multi-state article is in and/or the change of state of such an article; by way of example, detecting when an article is in a first state (e.g. a closed, return, reset, non-actuated, unopened or unused state) and/or in a second state (e.g. an open, primed, actuated or used state) and/or when there is a change from the first state to the second state and/or vice-versa. This is particularly the case where (i) a change of state results in, or is indicative of, an event occurring which it is desirable to monitor, and/or (ii) a correct usage of the article requires the article to follow a particular sequence of change of state (e.g. for the event to occur properly or for the indication being of the event occurring properly). This may be particularly important where the change of state of the article is by manually operation; i.e. its correct use (e.g. operation and/or time of use etc.) is user dependent, such as the case with hand-operable articles, which may be of the hand-held type (sized to be held in the hand, for operation and/or use thereof).

Such detection is particularly, but not exclusively, useful for multi-use, multi-state articles; i.e. articles which are repeatedly used and so moved repeatedly between its various states (e.g. by back-and-forth, reversible or reciprocal movement). For instance, some articles are repeatedly moved between opened and closed states (e.g. so as to enable access to contents therein when present) or repeatedly moved between non-actuated and actuated states (e.g. to dispense content therefrom or make content therein available, when the content is present), etc. Such state detection information can be used to form a usage history for the article; for instance: the number of times the article is used; the sequence of states the article is moved through to assess if the right sequence is followed for a correct usage event (or if it's a misuse event); etc. Moreover, where the article should be used according to a prescribed timetable, a usage history can be used to assess compliance of the article's usage to that timetable (through the addition of time-of-use information to the usage history).

As indicated previously, the detection of a usage history for a multi-use article may be particularly important where the change of state of the article is by manually operation; i.e. its correct use (e.g. operation and/or time of use etc.) is user dependent, such as in the case with a hand-operable, multi-use article, which article may be of the hand-held type too.

Specific non-limiting examples of such multi-use, multi-state articles are dispensers which contain, or are adapted to contain, a supply of something which is to be dispensed (or made available for dispensing) over the course of a number of uses until the supply is empty (or is deemed empty), particularly dispensers that need to be operated in a set sequence of operation steps and/or to be used with a supply of something which is to be used according to a prescribed timetable, for instance a dispenser for a supply of material comprising a pharmaceutical (drug, biopharmaceutical, vaccine, or anything else containing one or more substances with properties for treating, preventing, palliating or diagnosing disease in human beings (including symptomatic treatment)) having a prescribed dosing regimen. Typically, such dispensers have a non-actuated state and actuated state, the movement from the former to the latter resulting in a quantity of the supply (when present) to be dispensed or made available for dispensing. Inhalers are exemplary dispensers of this type, including pressurised metered dose inhalers (pMDI)—where the pharmaceutical is an aerosol formulation including a propellant—and dry powder inhalers (DPI)—where the pharmaceutical is in dry powder form. Such types of inhalers typically have a mouthpiece and are used for delivery of a pharmaceutical to a patient's lungs (a pulmonary inhaler), although it is possible to have such inhalers with a dispensing outlet configured as a nasal nozzle instead of a mouthpiece so as to deliver the pharmaceutical into the patient's nose (nasal inhaler). A pulmonary inhaler typically is used with a pharmaceutical for treating a respiratory disease or condition (such as asthma or COPD, and usually via topical action of the pharmaceutical in the lung), although such inhalers may also be used for delivery of a pharmaceutical for treating a disease or condition by systemic effect via the lungs, e.g. diabetes treatment by pulmonary delivery of insulin. Nasal inhalers may deliver a pharmaceutical for treating diseases or conditions related to the nose, such as rhinitis, or for systemic delivery or delivery across the blood-brain barrier.

As is known, such inhalers are typically hand-held and hand-operable. A pMDI typically requires the inspiratory effort of the patient at the dispensing outlet to be coordinated with the hand-operation of the pMDI so that a metered dose is dispensed into, and entrained, with the airflow through the pMDI for delivery to the pulmonary tract or nose, as applicable. This is known as a breath-coordinated pMDI. However, to resolve the potential issue of poor user coordination, there are also known breath-operated pMDIs in which the pMDI is primed and then 'fired' when the patient inhales at the dispensing outlet.

A DPI has the same uses as described above a pMDI, but avoids the need for a propellant which can be environmentally unfriendly through use of a dry powder. As there is no propellant, most DPIs rely on the inspiratory effort of the patient to draw the pharmaceutical out of the dispensing outlet (breath actuation), although there are some DPIs with breath-triggered mechanisms to assist release of the powder into the inspiratory airflow.

The dispensers of the type indicated above, including the inhalers, are typically manually-operable (especially hand-operable), and often hand-held. This is also the case for the types of inhaler to be discussed in greater detail herein.

A first type of dispenser of the kind mentioned above may include a supply in bulk form and a mechanism for dispensing or making available a portion of the bulk per actuation event. Where the supply is a pharmaceutical, the mechanism will typically be a metering mechanism for metering a dose from the supply for dispensing. Examples of pulmonary inhalers of this type are pMDIs, such as the EVOHALER pMDIs used by the GlaxoSmithKline group of companies in approved inhalation products such as the ADVAIR/SERETIDE EVOHALER inhaler product, and reservoir-type multi-dose DPIs (rDPIs), examples being the TURBU-HALER inhaler (AstraZeneca) and the EASYHALER (Orion Corporation).

A second type of dispenser of the kind mentioned above is loaded with a pre-prepared, sub-divided supply and includes a mechanism for dispensing or making available for dispensing a sub-division of the supply upon each actuation. Typically, where the supply is a pharmaceutical it is supplied as pre-metered doses. Examples of inhalers of this type are multi-unit-dose DPIs (mDPI) in which the pharmaceutical (in the form of an inhalable medicament powder) is pre-metered on a carrier as discrete doses (during the manufacturing process) and then loaded in the mDPI; the mechanism is adapted in use to index the carrier to present the discrete doses serially to an airflow path in communication with a mouthpiece of the inhaler. This may also be referred to as a factory-metered mDPI. Examples of such pulmonary mDPIs are the ELLIPTA inhaler and the DISKUS/ACCUHALER inhaler (both GlaxoSmithKline), and the GYROHALER (Vectura Group PLC).

The ELLIPTA inhaler is described in detail in inter alia WO2007/012871 (FIGS. 3 to 13, inclusive, and the related description) and WO2007/068896 (FIGS. 4 to 17, inclusive, and the related description), the entire contents of which are incorporated herein by reference. The ELLIPTA inhaler is used in the approved inhalation products BREO/RELVAR ELLIPTA, ANORO ELLIPTA, ARNUITY ELLIPTA and INCRUSE ELLIPTA marketed by the GlaxoSmithKline group of companies.

The ELLIPTA inhaler is able to work with one or two medicament carriers therein. When there is just a single medicament carrier in ELLIPTA, as in the ARNUITY ELLIPTA and INCRUSE ELLIPTA inhalation products, each actuation of the inhaler results in the inhaler mechanism indexing the medicament carrier to present a metered dose on the carrier to a position where it can be inhaled through the mouthpiece by the patient. When the ELLIPTA inhaler contains two medicament carriers, such as in the BREO/RELVAR ELLIPTA and ANORO ELLIPTA inhalation products, each actuation of the inhaler results in the inhaler mechanism indexing both medicament carriers to present a metered dose of each carrier to a position where they are able to be inhaled simultaneously through the mouthpiece by the patient. In this latter case, the metered dose delivered to the patient is the combination of the metered doses from each carrier (the powder on the first carrier containing a medicament powder having a different active pharmaceutical ingredient (API) or API mixture than that in the medicament powder of the second carrier).

The ELLIPTA inhaler has an 'open-inhale-close' actuation sequence. In other words, the ELLIPTA inhaler has a closed state (in which the mouthpiece is closed by a mouthpiece cover) and an open state (in which the mouthpiece is no longer closed), with movement from the closed state to the open state resulting in the inhaler mechanism indexing the carrier(s) so that a metered dose of medicament powder is available for inhalation through the mouthpiece. Thus, it will be appreciated that it can be useful to detect when the ELLIPTA inhaler is opened as that event is a surrogate for a metered dose being inhaled by a patient (opening being a condition precedent for inhalation of a metered dose). The use history of the ELLIPTA inhaler can be used for monitoring the compliance of the patient with the prescribed dosing regimen for the pharmaceutical product, which for the marketed products mentioned hereinabove is a once-daily (one metered dose per 24 hour period) dosing regimen. It will be appreciated that this logic applies generally to the use history of any article having an open-use*-close operating sequence (*non-exhaustive examples of "use" being ready-for-use or primed (as for the ELLIPTA inhaler) and automatic dispensing upon opening).

The opening and closing of the ELLIPTA inhaler is the patient moving the inhaler's mouthpiece cover from its closed position, in which it covers the mouthpiece, to an open position, in which the mouthpiece is opened and mouthpiece cover caused the inhaler mechanism to index the carrier(s) so that a metered dose is available for inhalation by the patient. Proper usage of the ELLIPTA inhaler involves reciprocal movement of the mouthpiece cover between its fully closed and fully opened positions (i.e. full stroke positions). However, the inhaler can also be operated correctly by moving the mouthpiece cover to positions short of these full stroke positions, due to the nature of the inhaler mechanism. It would therefore be useful to detect whether or not the mouthpiece cover, when opened or closed, has moved sufficiently far to the open or closed position, as the case may be, for the inhaler to be deemed to have been operated correctly by the patient. A misuse event can therefore be detected; e.g. by detecting that the mouthpiece cover has been moved insufficiently far in one direction and/or the other during a use event cycle that the inhaler will not have been operated correctly in that use event cycle.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

According to an aspect of the invention there is provided a multi-state article which comprises a sensor for sensing when the article is in at least a first one of its states, the sensor comprising a system of coils (coil system) which is adapted to provide a coil coupling which is representative of the first state when the article is in the first state. The coil system may further be adapted to provide a coil coupling which is representative of a second state (different from the first state) of the article when the article is in the second state.

According to another aspect of the invention there is provided a multi-state article which comprises a sensor for sensing when the article is in at least a first one of its states, the sensor comprising a system of coils (coil system) which is able to adopt different coil configurations, the coil system having a first coil configuration which is adopted when the article is in the first state and which is able to provide a coil coupling which is representative of the first state. The coil system may further have a second coil configuration which is adopted when the article is in a second state (different from the first state) of the article and which is able to provide a coil coupling which is representative of the second state. Preferably, movement of the article to the first state causes the coil system to adopt (e.g. move to) its first coil configuration; likewise, where there is the second coil configuration associated with the second article state, preferably movement of the article to its second state causes the coil system to adopt (e.g. move to) the second coil configuration. In embodiments, movement of the article between its first and second states causes the coil system configuration to move to the coil configuration which corresponds to the respective article state.

According to another aspect of the invention there is provided a multi-state article which comprises a sensor for sensing when the article is in at least a first one of its states, the sensor comprising a near-field communication (NFC) antenna. The sensor may include a signal generator adapted to produce a signal when the article is in said first state which is representative of the article being in the first state. The signal generator may be a coil in a system of coils (coil system) which includes or is an NFC antenna. The sensor (or coil system) may be as otherwise described herein.

According to another aspect of the invention there is provided an article having a prescribed usage regime which comprises an adherence sensor for sensing article use events and storing a use event history, the sensor comprising a NFC antenna for wireless transfer of the use history. The sensor may be as otherwise described herein. The article may as otherwise described herein and/or articles to dispense a supply of (e.g. pharmaceutical) substance having a prescribed dosing regime.

According to another aspect of the invention there is provided a method of sensing at least a first state of a multi-state article according to other aspects of the invention comprising the steps of moving the article to the first state so the sensor senses the first state (e.g. produces the signal/coil coupling which is representative of the first state). In embodiments the article is moved repeatedly back-and forth to the first state so the sensor senses the first state at each instance thereof. In embodiments the article is moved to a second state, optionally repeatedly, so the sensor senses the second state (e.g. produces the signal/coil coupling representative of the second state). In embodiments the article is repeatedly moved back-and-forth between the first and second states. In embodiments the method further comprises the step of storing data relating to the sensed state (e.g. coil coupling(s)/signal) in memory on the sensor. In embodiments, the method includes the step of creating data relating to the time a state is sensed (e.g. the time (or period of time) when the state is changed) and including that time data in the stored data (i.e. associating the time data with the associated state data in the stored data). In embodiments the method comprises transferring (conveniently wirelessly) the stored data to a remote computer device (e.g. a smartphone/tablet/such-like (or App thereon)). In embodiments the data transfer is by NFC.

NFC

The NFC antenna enables wireless communication between the sensor and another NFC-enabled article, e.g. a NFC reader, such as an NFC-enabled portable device like a smartphone, tablet or such-like. Thus, sensor data may be communicated to another NFC-enabled article. The sensor data may be the use event history (supra) and/or (other) data stored in memory of the sensor. The use event history may comprise state information (which state has been sensed) and data representative of the time (or period of time) of sensing of use events of the article (e.g. time of sensing of a given state). Such use event history can be compared to e.g. a prescribed usage regime.

In embodiments the sensor comprises an NFC electronic circuit.

Sensor

In embodiments the sensor is an electronic sensor, preferably at least part of which is printed. As an example, the coil system may be printed.

In embodiments the coils adopt a spatial arrangement with respect to each other when the article is in its first state which is different to the spatial arrangement adopted when the article is not in the first state (i.e. in other article states and intermediate states). In embodiments, the coils adopt respective first and second (different) spatial arrangements with respect to each other in the first and second article states. Typically, the coils are caused to move between the first and second spatial arrangements by movement of the article between its first and second states.

In embodiments the sensor includes a movable first coil which moves with respect to the other coil(s) as the article moves between its different states. Typically, the other coil(s) are in fixed positions. The movable first coil may be movable between first and second positions, the first of which is the position of the movable first coil in the first state of the article (the second of which may be the position of the movable first coil in the second state). In embodiments the movement of the movable first coil between its first and second positions moves the coil system between the first and second spatial arrangements. In embodiments the coil system has second and third coils and in the first position the movable first coil is disposed adjacent to the second coil for a coupling therewith representative of the article being in the first state. In embodiments in the second position the movable first coil is disposed adjacent the third coil for a second coupling therewith which is representative of the article being in the second state.

In embodiments the article comprises (a) a first structure which (i) in the first state has a first position and in a/the second state has a second position, and (ii) is provided with at least one coil of the coil system (e.g. the afore-mentioned movable first coil) of the sensor; and (b) a second structure which is provided with the rest of the coil system of the sensor; and the first and second structures are movable relative to one another to move the article between its first state and a/the second state and to change the position of the least one coil relative to the rest of the coil system to change the coupling in the coil system (e.g. between the at least one coil and a coil of the rest of the coil system) thereby to sense when the article is in its first state and, optionally, its second state. Typically, the rest of the coil system on the second structure has a fixed position.

In embodiments the sensor comprises three coils, a first one of which is movable with respect to the other two to provide (i) the coil coupling representative of at least the first state, or (ii) the coil couplings representative of the first and second states, or (iii) the different (e.g. first and second) spatial arrangements for the coils. The first coil may be the afore-mentioned movable first coil and/or the first coil on the first structure of the article (in the latter case, the other two coils being comprised in the coil system on the second structure). In embodiments the coil coupling between the moving first coil and a first one of the other coils is to sense the article being in the first state and the coil coupling between the moving first coil and the second one of the other coils is to sense the article being in the second state. Typically, the other two coils have fixed positions.

In embodiments the coil system comprises a driver coil, a detector coil and a moving coil (e.g. as detailed above). When the moving coil is in a first position, corresponding to the first state of the article, the driver coil is able to couple with the detector coil through the moving coil to provide a coupling with the detector coil which is representative of the first state. In effect, the moving coil forms a coupling bridge from the driver coil to the detector coil. In embodiments when the moving coil is in a second position, corresponding to a/the second state of the article, the moving coil couples with the driver coil to provide a coupling which is representative of a/the second state of the article. In embodiments, when the moving coil is not in the first position (i.e. the article is not in the first state) the coupling of the driver and detector coils is different and so representative that the article is not in the first state. Likewise, in embodiments, when the moving coil is not in the second position (i.e. the article is not in the second state) the coupling of the driver and moving coils is different and so representative that the article is not in the second state. Typically, the driver and detector coils are in fixed positions.

In embodiments, the driver coil is also a/the NFC antenna.

In embodiments the coil system comprises a first coil (e.g. the driver coil supra) for producing a magnetic field (e.g. at a RF frequency or NFC protocol frequency) for inductive coupling with at least a second coil (e.g. the moving coil supra) of the coil system, the inductive coupling between the coils being dependent on the state of the article; e.g. dependent on whether or not the article is in the first state and/or dependent on the relative positioning of the coils which are determined by the state (and optionally also intermediate states) of the article.

In embodiments the second coil is movable between first and second positions relative to the first coil and to a third coil (e.g. the detector coil supra) of the coil system to provide differential inductive coupling at the third coil. As an example, in the first position of the second coil, corresponding to the first state of the article, the inductive coupling in the third coil is at a first level, and in the second position of the second coil, corresponding to a/the second state of the article, the inductive coupling in the third coil is at a second level which is different from (e.g. lesser than) the first level. Typically, the first and third coils are in fixed positions (e.g. on the second structure of the article, supra).

In embodiments, the second coil is positioned closer to the third coil when in the first position than in the second position. For example, in the first position the second coil is in close proximity to the third coil (and optionally also to the first coil) and in the second position is remote from the third coil. In embodiments, the first and second coils are in close proximity to one another in the first position and/or the second position of the second coil.

In embodiments, the configuration and arrangement of the coils is such that the first coil is able to inductively couple with the second coil in both its first and second positions and the second coil is able to inductively couple with the third coil when in its first position, such inductive coupling in the third coil being greater than any inductive coupling in the third coil from the first and second coils when the second coil is in its second position.

In embodiments the second/moving coil in its first position is disposed between the first/driver coil and the third/detector coil; e.g. in a bridging disposition.

In embodiments, in the second position of the second/moving coil the first/driver coil is positioned between the second/moving coil and the third/detector coil.

In embodiments, when the article moves from its first state to the second state the first coil (also referred to as the moving coil in some statements herein) moves closer to a first one of the other coils (the second coil; e.g. the third/detector coil in other statements herein) and vice-versa. Expressed another way, the first coil is movable from a first position (corresponding to the article's first state), at which the first coil is at a first spacing from a first one of the other coils (the second coil), to a second position (corresponding to the article's second state), at which the first coil is at a second spacing, greater than the first spacing, from the second coil. In embodiments, the first coil is proximate the second one of the other coils (the third coil; e.g. the first/driver coil in other statements herein) in both the first and second states of the article (i.e. the first coil remains proximate to the third coil as the first coil moves during the transition of states of the article and/or the first coil moves between its first and second positions. In embodiments, the second and third coils are in fixed positions (i.e. do not move with respect to each other as the article moves between its first and second states). In embodiments the first coil is positioned between (e.g. like a bridge) the second and third coils in the first state of the article and/or first position of the first coil. In embodiments, in the second state of the article or the second position of the first coil, the first coil is either not between (e.g. does not bridge) the second and third coils or is between the second and third coils to a lesser degree than when in the first state of the article or first position of the first coil, respectively. Typically, the second and third coils are in fixed positions.

In embodiments the sensor comprises first, second and third coils, the first coil is provided to a first structure of the article and the second and third coils are provided to a second structure of the article, the first and second article structures are relatively movable (e.g. by movement of one structure with respect to the other) to provide first and second positions of the first article structure with respect to the second article structure corresponding, respectively, to the first and second states of the article. The coils may be as described herein, e.g. the moving coil is on the first structure and the other coils (e.g. driver and detector coils) are on the second structure, and they interact as previously described when the article is in its first and second states.

In embodiments the sensor is an electronic device which comprises a memory to store sensor data representative of the states sensed and optionally time data associated with the state data.

In embodiments the coil system is adapted in use to produce signals representative of the state sensed. In embodiments the signals (or a processed form thereof) are stored in a/the memory of the sensor. In embodiments the sensor includes an electronic circuit to process the signals.

Article

In embodiments the first state of the article is (a) one or more of a closed, return, reset, non-actuated, unopened or unused state or (b) one or more of an open, primed, actuated or used state. In embodiments the first state is (b). In embodiments the second state is whichever of (a) and (b) the first state is not. In embodiments the first state is an open state (optionally also an actuated state) and the second state is a closed state (optionally also a non-actuated state), or vice-versa.

In embodiments the article is manually (hand-) operable to effect its change of state.

In embodiments the article is a hand-held article.

In embodiments the article is a multi-use, multi-state article. The multi-use article may be movable repeatedly between its states by back-and-forth, reversible or reciprocal movement, for instance repeatedly movable between closed and opened states (e.g. so as to enable access to contents therein when present) or repeatedly movable between non-actuated and actuated states (e.g. to dispense content therefrom or make content therein available, when the content is present).

In embodiments the article is a multi-use, multi-state dispenser which contains or is adapted to contain a supply of something which is to be dispensed or made available for dispensing over the course of a number of uses until the supply is empty or is deemed empty. The dispenser may be of the type that needs to be operated in a set sequence of operation steps and/or to be used with a supply of something which is to be used according to a prescribed timetable, for instance a dispenser for a supply of material comprising a pharmaceutical having a prescribed dosing regimen. Typically, the states of a dispenser are a non-actuated and/or closed state and an actuated and/or open state, the movement from the former to the latter resulting in a quantity of the supply (when present) to be dispensed or made available for dispensing.

In embodiments the dispenser is an inhaler, for instance a pressurised metered dose inhaler (pMDI) or a dry powder inhaler (DPI), as discussed above in the 'Discussion of the Background' section supra. Typically, an inhaler is hand-held and hand-operable.

In embodiments the inhaler is a multi-dose DPI, for example a reservoir DPI or a multi-unit-dose DPI (again, see the 'Discussion of the Background' section supra). In embodiments the multi-dose DPI has an 'open-inhale-close' operation sequence (a closed state in which the dispensing outlet (e.g. mouthpiece) is closed by a cover) and an open state (in which the dispensing outlet is no longer closed), with movement from the closed state to the open state resulting in the inhaler mechanism making a metered dose of medicament powder available for dispensing through the dispensing outlet. Thus, it will be appreciated that it can be useful to detect when the multi-dose DPI is opened as that event is a surrogate for a metered dose being administered by a patient (opening being a condition precedent for administration of a metered dose). The use history of the multi-dose DPI may be used for monitoring the compliance of the patient with the prescribed dosing regimen for the pharmaceutical product, which for example may be a once-daily (one metered dose per 24 hour period) dosing regimen.

It will be appreciated that the above logic applies generally to the use history of any article having an open-use*-close operating sequence (*non-exhaustive examples of "use" being ready-for-use or primed and automatic dispensing upon opening). Thus, in embodiments, the article has an open-use-close operating sequence with the article states corresponding to closed and open states.

In embodiments the article has an outlet and a closure (e.g. cover) therefor and the article is moved between closed and open states by moving the closure from a closed position, in which it closes the outlet, to an open position, in which the outlet is opened. The closure may be moved repeatedly between its closed and open states, e.g. by reversible movement.

In embodiments the article first structure is the closure and the article second structure is a body of the article on which the closure is mounted for movement to change the state of the article.

In embodiments the article is an inhaler and the closure is a mouthpiece cover and actuator of the inhaler.

The present invention further relates to electronic devices and methods of manufacturing and using the same. The present invention relies on multiple antennas that are brought in proximity to induce positive feedback, resulting in oscillation or a change in state of a bistable device. The oscillation or change in state can be used to determine the state of the device.

In one aspect, the present invention relates to an electronic device, comprising a first substrate with first and second coils thereon, and a second substrate with a third coil thereon. The first coil has an integrated circuit electrically connected thereto, and the first substrate is a first part of an article, container or product packaging or is configured to be attached or secured to the first part of the article, container or product packaging. The second substrate is a second part of the article, container or product packaging, or is configured to be attached or secured to the second part of the article, container or product packaging. One of the first and second parts of the article, container or product packaging is removable or movable with respect to the other one of the first and second parts of the article, container or product packaging. The first and second coils have a first coupling when the article, container or product packaging is closed or sealed, and a second, different coupling when the article, container or product packaging is open or unsealed. In some embodiments, the first substrate may comprise one or more parts, and the first and second coils may be on the same part or different parts. In either case, the first and second coils are in fixed positions relative to each other.

In many embodiments of the electronic device, the first, second and third coils form a continuity sensor. The continuity sensor senses or determines a continuity state of the container or product packaging. In some cases, the first coupling corresponds to a closed or sealed continuity state, and the second coupling corresponds to an open or unsealed continuity state. Alternatively, the first coupling corresponds to the open or unsealed continuity state, and the second coupling corresponds to the closed or sealed continuity state. In further embodiments, the first and second coils can have a third coupling when the article, container or product packaging is partially open or not fully closed or sealed. In general (but not necessarily always), the third coupling is between the first coupling and the second coupling.

In some embodiments, one of the first and second parts of the article, container or product packaging may be removable or movable with respect to the other one of the first and second parts of the article. In a further embodiment, the removable or movable part is repeatedly movable between the open and closed continuity states. For example, a repeatedly movable part of the article, container or product packaging may be or comprise a cap or lid connected to the article or container by a hinge, a pivot or spindle, one or more tongue-in-groove fittings, etc.

In some embodiments of the electronic device, the continuity sensor further comprises a transistor electrically coupled directly or indirectly with at least one of the first and second coils. In some cases, the first, second and third coils form an open loop when the continuity sensor has the closed or sealed continuity state, and the third coil closes the loop when the continuity sensor has the open or unsealed continuity state. Alternatively, the first, second and third coils form a closed loop when the continuity sensor has the closed or sealed continuity state, and the third coil opens the loop when the continuity sensor has the open or unsealed continuity state. In further embodiments, the closed loop propagates an oscillating signal, and the open loop does not propagate the oscillating signal (e.g., from the first stationary coil to the second stationary coil).

In various embodiments, the second coil may have at least a first capacitor electrically connected thereto, and the third coil may have a second capacitor electrically connected thereto. In other or further embodiments, the electronic device further comprises a diode or other element or circuit such as an envelope detector configured to detect the oscillating signal (or a maximum value thereof). The electronic device (e.g., the integrated circuit) may further comprise one or more devices configured to provide a bias current at a source/drain terminal of the transistor coupled to the first and/or second stationary coils. In some cases, the bias current may be controlled by a gain control signal comprising a sequence of pulses having a predetermined duty cycle.

In some embodiments, the continuity sensor may have a relatively high coupling state when the container or product packaging is closed or sealed, and a relatively low coupling state when the container or product packaging is open or unsealed. Alternatively, the continuity sensor may have a relatively low coupling state when the container or product packaging is closed or sealed, and a relatively high coupling state when the container or product packaging is open or unsealed.

In various embodiments, the electronic device may further comprise a battery configured to provide power to the integrated circuit. In other or further embodiments, the integrated circuit may comprise a rectifier configured to extract power from a wireless signal received by the first coil. The integrated circuit may also comprise a closed state detector and an open state detector. Each of the closed state and open state detectors may comprise an amplifier configured to amplify an output from a corresponding stationary coil, an envelope detector configured to determine a maximum value of an output from the corresponding amplifier, and a latch coupled directly or indirectly to an output of the envelope detector and configured to store the maximum value of the output from the corresponding amplifier.

In many embodiments, the integrated circuit comprises a printed integrated circuit. Printing is generally a high-throughput, additive technology that minimizes wasteful application of materials that must be subsequently removed, and avoids the use of expensive, low-throughput equipment such as photolithography equipment.

In another aspect, the present invention relates to an article, package or container, comprising first and second parts with an interface therebetween, where one of the parts is separable or movable with respect to the other. The first substrate of the present electronic device is, or is on, one of the parts of the article, package or container, and the second substrate is, or is on, another part (e.g., the other one of the first and second parts) of the article, package or container.

In some embodiments, the article, package or container is considered open when the first and second coils have the second coupling, and the package or container is considered closed or sealed when the first and second coils have the first coupling. For example, the third coil is closer to the first coil than to the second coil when the container or package is closed or sealed, and when the container or product packaging is open or unsealed, the third coil is (i) absent or (ii) closer to the second coil than when the container or package is closed or sealed. Alternatively, the article, package or container may be considered closed or sealed when the first and second coils have the second coupling, and the package or container may be considered open when the first and second coils have the first coupling.

In yet another aspect, the present invention relates to a method of detecting a continuity state of an article, package or container, comprising placing first and second coils on a first part of the article, package or container, placing a third coil on a second part of the article, package or container, and sensing the continuity state of the article, package or container using the first, second and third coils. One of the first and second parts of the article, container or package is removable or movable with respect to the other one of the first and second parts of the container or product packaging. The first coil has an integrated circuit electrically connected thereto. The first and second coils have a first coupling when the article, package or container is closed or sealed, and a second, different coupling when the article, package or container is open or unsealed.

In various embodiments of the method, the article, package or container is considered open or unsealed when the first and second coils have the second coupling, and the article, package or container is considered closed or sealed when the first and second coils have the first coupling. Alternatively or additionally, the third coil may be closer to the first coil than to the second coil when the article, container or package is closed or sealed, and the third coil is (i) absent or (ii) closer to the second coil than when the article, container or package when the article, container or product packaging is open or unsealed.

As for the continuity sensor and article, package or container, the first, second and third coils may form a continuity sensor in the present method. The continuity sensor senses or determines the continuity state of the article, container or package. In some examples, the first coupling corresponds to a closed or sealed continuity state, and the second coupling corresponds to an open or unsealed continuity state. In other or further examples, the first, second and third coils may form a loop (which may be a feedback loop) when the continuity sensor has the closed or sealed continuity state, and the third coil breaks the loop when the continuity sensor has the open or unsealed continuity state. In some embodiments of the method, the loop propagates an oscillating signal when the continuity sensor has the closed or sealed continuity state, and does not propagate the oscillating signal when the continuity sensor has the open or unsealed continuity state. Alternatively, the opposite arrangements are also possible (i.e., the first coupling corresponds to an open or unsealed continuity state, and the second coupling corresponds to a closed or sealed continuity state; the first, second and third coils may form a loop when the continuity sensor has the open or unsealed continuity state, and the third coil breaks the loop when the continuity sensor has the closed or sealed continuity state; and/or the loop propagates the oscillating signal when the continuity sensor has the open or unsealed continuity state, and does not propagate the oscillating signal when the continuity sensor has the closed or sealed continuity state). In one example, the method further comprises detecting the oscillating signal with the open state detector when the continuity sensor has the open or unsealed continuity state.

Further embodiments of the method may further comprise applying a bias current at a source/drain terminal of a transistor coupled to the first stationary coil, controlling the bias current with a gain control signal comprising a sequence of pulses having a predetermined duty cycle, providing power to the integrated circuit using a battery and/or receiving a wireless signal at the first stationary coil. When the method comprises receiving the wireless signal at the first stationary coil, the method may further comprise extracting power from the wireless signal with a rectifier (which may be part of the integrated circuit). As for the present continuity sensor and article, container or package, the integrated circuit may comprise a printed integrated circuit.

It will be understood that the different aspects of the invention may include embodiments based on the disclosure in the 'Discussion of the Invention' section, including without limitation any of the details on articles discussed therein and/or desired aims.

The present invention further includes combinations of each aspect of the invention and its embodiments with part or all of the content of any one or more of the other aspects or its embodiments, including the embodiments hereinafter to be described with reference to the Figures of drawings.

In the present specification the terms "article", "device" and "product" are interchangeable except in instances where this would clearly not be the case.

The present invention advantageously avoids any need to tear or break a wire when a container or product packaging is opened to determine its continuity state (e.g., whether it is "opened" or "closed"), and thus avoid issues that sometimes arise with product security and authentication technology that relies on tearing or breaking a wire. In some embodiments, the present invention is capable of sensing multiple continuity states as well as sensing a continuity state times (e.g., 10 or more times, 20 or more times, 30 or more times, 100 or more times, etc.) using two active (e.g., battery-powered) coils to generate electromagnetic fields, and a passive coil passing through the two fields to provide a voltage difference. These and other advantages of the present invention will become readily apparent from the detailed description of various embodiments below.

BRIEF DESCRIPTION OF THE DRAWINGS

FIG. 1 is a schematic for an exemplary 3-coil continuity sensor according to embodiments of the present invention.

FIGS. 6A-F are views of an exemplary prototype 3-coil continuity sensor according to one or more embodiments of the present invention.

FIGS. 7A-F are plots showing voltage on one coil of the exemplary prototype 3-coil continuity sensor of FIGS. 6A-F as a function of the location of another coil of the exemplary prototype 3-coil continuity sensor of FIGS. 6A-F.

DETAILED DESCRIPTION

Figure 2A:
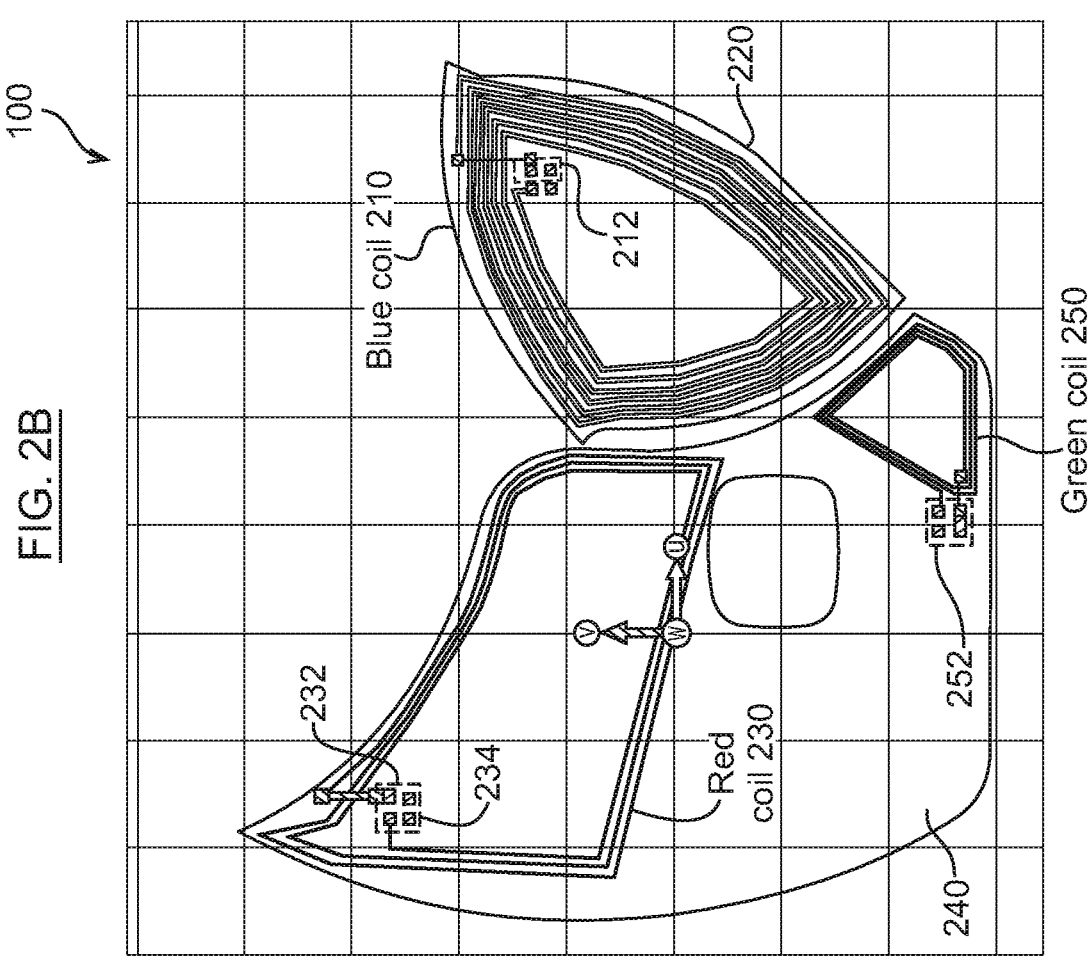
FIGS. 2A-B are diagrams showing an exemplary design for a 3-coil continuity sensor according to one or more embodiments of the present invention.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures and components have not been described in detail so as not to unnecessarily obscure aspects of the present invention. Furthermore, it should be understood that the possible permutations and combinations described herein are not meant to limit the invention. Specifically, variations that are not inconsistent may be mixed and matched as desired.

The technical proposal(s) of embodiments of the present invention will be fully and clearly described in conjunction with the drawings in the following embodiments. It will be understood that the descriptions are not intended to limit the invention to these embodiments. Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise.

In the various drawings, use of like reference numerals indicates like features, but the use of dissimilar reference numerals does not necessarily indicate dissimilar features.

For the sake of convenience and simplicity, the terms "part," "portion," and "region" are, in general, interchangeable and may be used interchangeably herein, but are generally given their art-recognized meanings. Wherever one such term is used, it also encompasses the other terms. In addition, the terms "antenna" and "coil", are used interchangeably, and where one term is used, it may also encompass the other term, but these terms are also generally given their art-recognized meanings. Also, unless indicated otherwise from the context of its use herein, the terms "known," "fixed," "given," "certain" and "predetermined" may be used interchangeably and generally refer to a value, quantity, parameter, constraint, condition, state, process, procedure, method, practice, or combination thereof that is, in theory, variable, but is typically set in advance and not varied thereafter when in use.

The present invention advantageously enables electrical devices to detect or determine the continuity state of a container or package (which may be a multi-use container or package) without any need to tear or break a wire. However, in some embodiments, the present invention can be used in conjunction with a product authenticity sensor (e.g., based on OpenSense™ technology commercially available from Thin Film Electronics ASA, Oslo, Norway) that includes a wire crossing an interface of the product packaging. A further option is the use of such a wire on a tab, the pulling/tearing of which breaks the wire and disconnects a "battery off" switch or battery disable circuit to save battery power until the product is actually used. Furthermore, the present invention allows use of conventional, relatively simple circuit elements, relatively simple electrical and/or electromagnetic phenomena, and conventional processing, thereby minimizing the cost of manufacturing and/or the development time for certain tags (e.g., wireless devices and/or "smart" labels) including the present electrical devices.

The present invention concerns an electronic device including a continuity sensor that wirelessly senses the continuity state of a container or product packaging. The device relies on two antennas or coils on a first part of the container or product packaging and a third coil on a second, separable first part of the container or product packaging. The third coil couples the two antennas or coils on the first part of the container or product packaging (e.g., when the container or product packaging is in one of a plurality of different states). In a typical embodiment, the two antennas or coils on the first part of the container or product packaging have relatively low coupling in the absence of the third antenna/coil or when the container or product packaging is in a different state. Thus, the two antennas or coils on the first part of the container or product packaging are brought together (e.g., by inductive coupling) to induce positive feedback resulting in an oscillation or change in state of the electronic device, which in one or more embodiments is a bistable device (e.g., a device having two stable states, such as the "open" and "closed" continuity states). The oscillation or change in state can be detected to determine the change of state in the electronic device (e.g., an RF or NFC tag), and hence, the change in the state of the article (e.g., from closed to open). The positive feedback can be generated by either electric or magnetic coupling.

One application of the present invention to product security and/or authentication involves a radio frequency (RF), near field communication (NFC) or other tag (e.g., a device that communicates using a wireless protocol such as Bluetooth and/or a predetermined frequency in the HF, VHF, UHF or RF band) on product packaging, in which two coils are placed on one part or component of the packaging, and the other coil is placed on another, separable part or component of the packaging. When the part or component of the product packaging containing the third coil is removed or separated, coupling between the remaining coils increases or decreases significantly (depending on the position of the third coil relative to the first two coils), which can be detected and used as a signal.

Another application of the present invention is directed towards detection of the continuity state of a multiple-use product or article, involving the radio frequency (RF), near field communication (NFC) or other tag on the product or article, in which two coils are placed on one part or component of product or article, and the other coil is placed on another, separable or separately movable part or component of the product or article. When the part or component of the product or article containing the third coil is moved relative to the two coils, a signal from one or both of the remaining coils changes significantly.

The present invention relies on multiple antennas/coils (typically three) to sense a continuity state (e.g., "open" or "closed") of a container or packaging containing a product (e.g., an authentic product). One of the antennas/coils moves, or changes its position relative to the other two antennas/coils, the positions of which generally remain fixed. The moving antenna/coil works in conjunction with the two fixed antennas. In a first continuity state 1 (e.g., "closed"), magnetic coupling between the fixed coils is small. However, in a second continuity state 2 (e.g., "open"), magnetic coupling between the fixed coils is increased due to the presence of the moving coil. Alternatively, this can work in the complementary way (i.e., in the first continuity state, magnetic coupling between the fixed coils is high due to the presence of the moving coil, and in the second continuity state, the magnetic coupling between the fixed coils is relatively small). This property may be used to construct continuity sensors that do not require physical connection (e.g., a wire) and that can be used and possibly re-used any number of times. Moreover, it may be possible to determine intermediate states between the first and second continuity states (e.g., to quantify the degree of container/package openness or security/continuity, to identify a "partially open" state, etc.).

The technique can be extended to the use of electric coupling instead of magnetic coupling.

FIG. 1 shows a continuity sensing system 100 that illustrates the basic principle behind the invention. The exemplary continuity sensing system 100 includes first and second stationary coils (e.g., red and green coils 102 and 104) and a third coil (blue coil 106) that changes position (e.g., that moves from one position proximate to the first coil 102, but relatively distant from the second coil 104, to another position closer to the second coil 104, but in which the center of the third coil 106 is relatively distant from the first coil 102). The proximity of the third coil 106 (e.g., the moving coil) increases coupling between the first and second coils 102 and 104 (e.g., the stationary coils). In absence of the third coil 106, coupling between the first and second coils 102 and 104 is low by design.

Continuity sensing generally refers to a capability and/or function that senses or determines whether an article, a container or product packaging is open (or, in the case of product authenticity and/or security, has been tampered with) on the one hand, or is closed (e.g., in the case of product authenticity and/or security, in its factory-sealed condition) on the other hand. Continuity sensing also includes in some cases determining whether the article, container or product packaging is partially open or has one or more of a plurality of parts or compartments that are open and one or more parts or compartments that are closed.

When determining the continuity state of the container or product packaging (e.g., when the electronic device is in an "open/closed" detection mode), none of the coils 102, 104 or 106 needs to receive a signal from a reader (assuming the electronic device in a tag on the container or product packaging is powered by an internal power source, such as an integrated or external battery). However, the first coil 102, and optionally the third coil 106 and/or the second coil 104, can participate in communicating information to the reader. Thus, the coils 102, 104 or 106 may have a dual role; that is, the same coils that enable open/closed state detection (e.g., that are in the continuity sensor) can also participate in NFC or other wireless communications. The open terminals on the first and second coils 102 and 104 are connected to other elements and/or components completing a circuit.

FIG. 2A shows a system 200 designed to demonstrate the feasibility of a continuity sensor based on one or more principles of the continuity sensing system 100 in FIG. 1. A third coil 210 on a first substrate 220 was placed in a first position in proximity to a first coil 230 on a second substrate 240. A second coil 250 was also on the second substrate 240. The first and second substrates 220 and 240 can be a label (e.g., a flexible plastic film that further includes an adhesive and that may further include graphics and/or one or more layers of paper and/or metallization), a backing sheet for electronics, etc. Alternatively, the first, second and third coils can be formed on and/or embedded in the product container/housing itself, and thus not on a separate substrate (e.g., the container may be the substrate for the first and second coils 230 and 250 and/or the third coil 210). Furthermore, the coils 210, 230 and 250 may be printed on the first and second substrates 220 and 240.

In various embodiments, the first coil 230, which can be involved in wireless signal reception/transmission, has an integrated circuit (IC; not shown, but which may be a printed IC on the same or a separate substrate, which may be a flexible substrate, such as a product label) coupled or electrically connected to it through the bonding pads 232 and one or more capacitors electrically connected to it and/or the IC through the bonding pads 232 and/or 234. Furthermore, the second coil 250 and the third coil 210 (which are generally not involved in wireless signal reception/transmission) may have one or more capacitors electrically connected to them through the bonding pads 252 and/or 212. The capacitor(s) connected to the second coil 250 may be part of a printed IC (PIC) that is generally (but not necessarily) separate from the printed IC coupled or electrically connected to the first coil 230. The capacitor(s) and/or PIC connected to the second coil 250 may be on the same or a separate substrate (which may be a flexible substrate, such as a product label) as the second coil 250. Alternatively, the capacitor connected to the second coil 250 may be an external component(s). The capacitor(s) connected to the third coil 210 are separate (e.g., an external component) because the third coil 210 is physically removed from the part of the container or product packaging on which the first and second coils 230 and 250 are located (e.g., the "main body" of a product container) or is otherwise physically relocated relative to the first and second coils 230 and 250. The capacitor(s) connected to the third coil 210 can be a standard part, implemented as a PIC or implemented as part of the third coil. In each case, the capacitor(s) coupled to the respective coil generally have a capacitance and/or other parameter values adapted to facilitate or enable resonance of the coil(s).

Figure 3A:
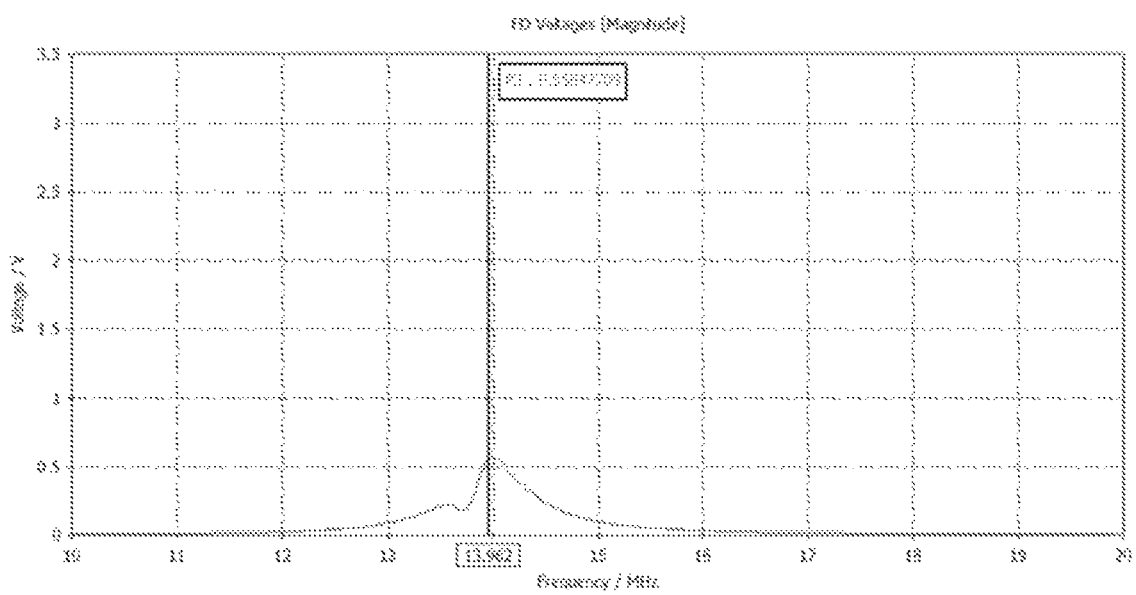
FIGS. 3A-B are plots showing voltage on a second stationary coil of the exemplary design of FIGS. 2A-B as a function of the location of a moving coil.

The third coil 210 was made to resonate at approximately 14 MHz, and an excitation was applied at the first coil 230. The voltage at the second coil 250 was monitored. FIG. 3A is a graph showing the voltage on the second coil 250, which was about 0.56 V (by simulation) at the resonant frequency.

Figure 2B:
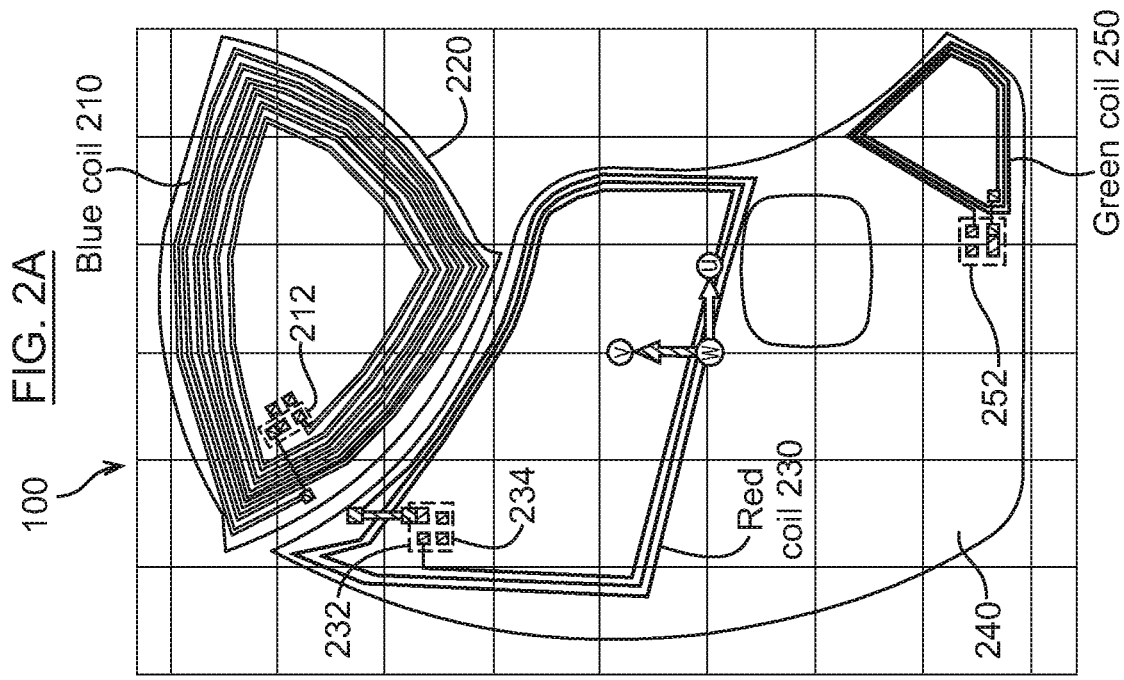
Figure 3B:
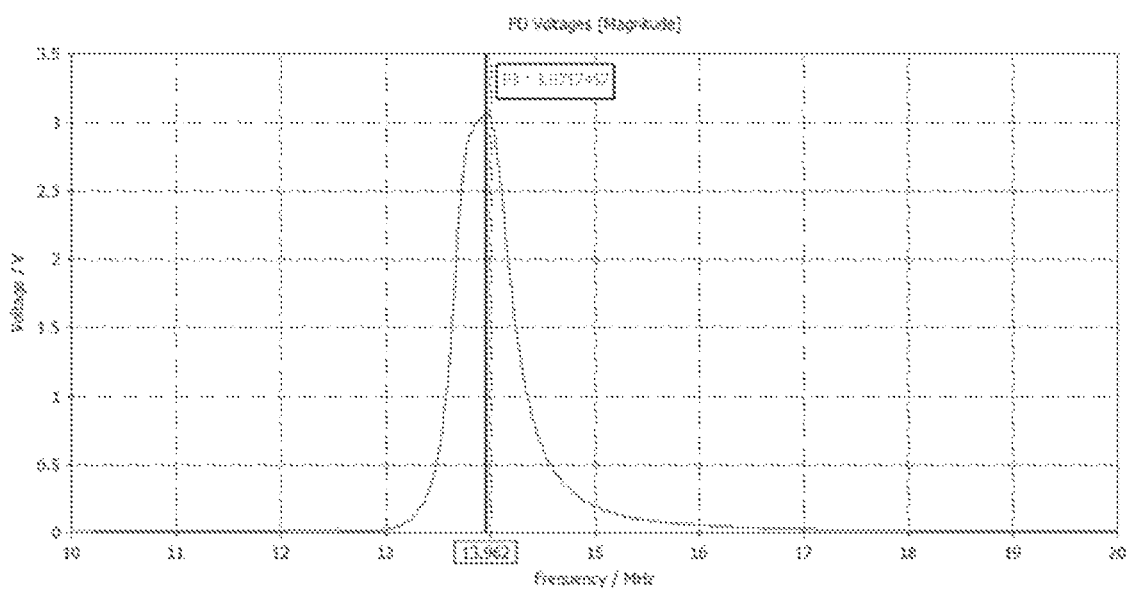

FIG. 2B shows the system 200 in which the third coil 210 is in a second, different position with respect to the red and green coils 230 and 250 (which remain in the same positions with respect to each other). The second position of the third coil 210 corresponds to a torn or opened product package or container. In the second position of the third coil 210, the first coil 230 is more strongly coupled to the second coil 250. As shown in the graph of FIG. 3B, the voltage on the second coil 250 was about 3.07 V (by simulation) when the third coil 210 was in the position shown in FIG. 2B, between 5 and 6 times the voltage on the second coil 250 when the third coil 210 is in the low-coupling state (e.g., as shown in FIG. 2A). Thus, the states of the bistable continuity sensor 200 can be characterized as a "high-coupling state" and a "low-coupling state."

In various embodiments of the invention, the high-coupling and low-coupling states of the system 200 correspond to different states (for example, different continuity states such as closed and open) of a container or product packaging with which the system 200 is associated (for example, by attachment to or incorporation in the product container or housing). In some embodiments, at least one component of the system 200 (e.g., part of the product container or packaging) is able to move repeatedly between different states as described above (e.g., back-and-forth), and consequently, can be associated with a product that has a feature that can be repeatedly movable between different states or positions so as to detect such changes of product state. Over time, a history of the product states can be compiled. This is particularly useful for determining compliance with a medical therapy or treatment regimen when the product is a medicine delivery article or system.

Figure 4:
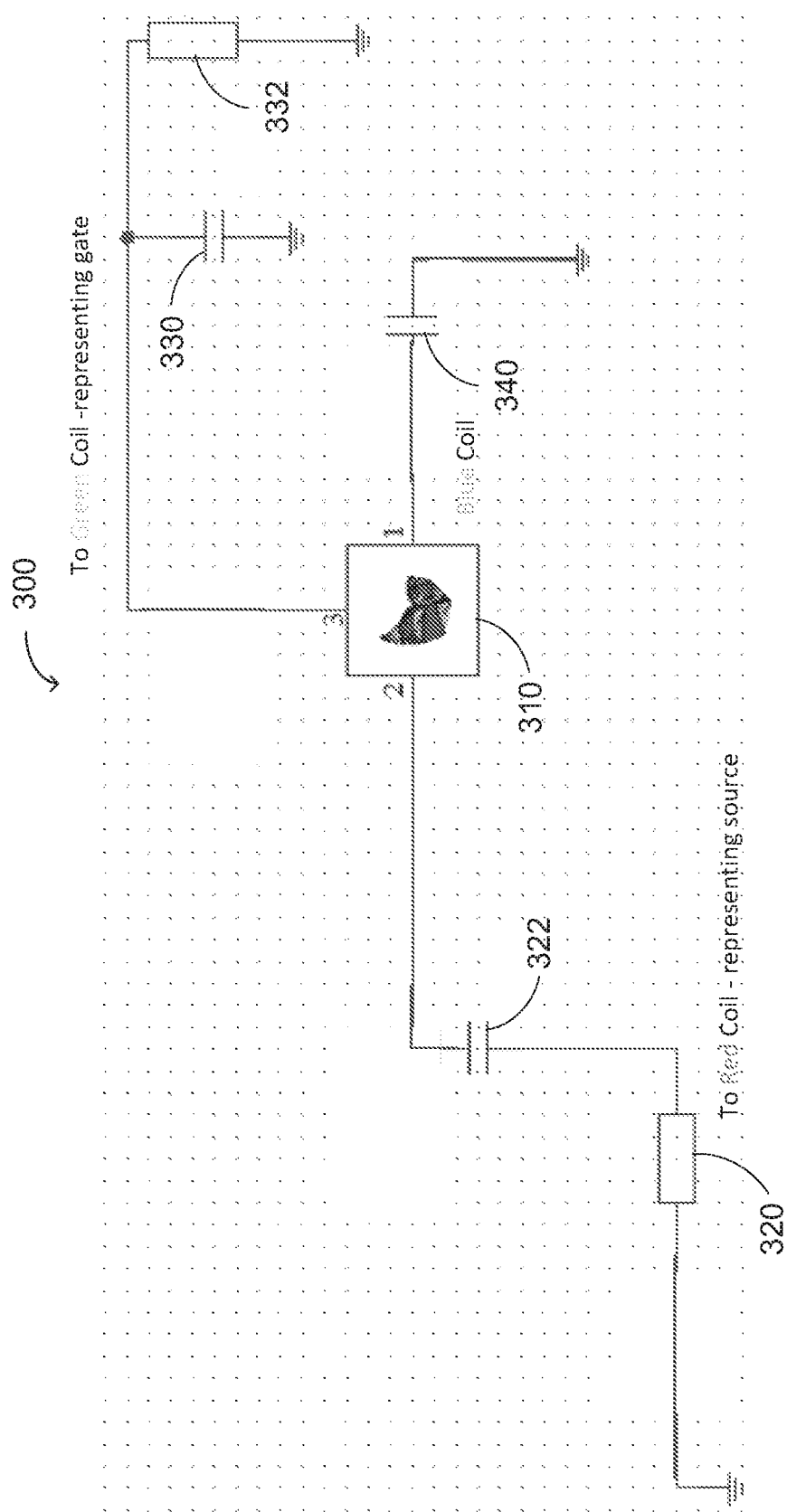
FIG. 4 is a schematic for an exemplary equivalent circuit for the 3-coil continuity sensor of FIGS. 2A-B.

FIG. 4 shows an equivalent circuit 300 for the system shown in FIGS. 1 and 2A-B. The equivalent circuit 300 includes a three-port circuit element 310, a first path to the first coil comprising a resistor 320 and a capacitor 322, a second path to the second coil comprising a capacitor 330 and a resistor 332, and a third path that includes or is to the third coil comprising a capacitor 340. The resistor 320 may have a resistance that is higher than (e.g., by 2-5×) the resistance of the resistor 332. The capacitor 322 may have a capacitance that is higher than (e.g., by 2-3×) the capacitance of the capacitor 340, and the capacitor 330 may have a capacitance that is higher than (e.g., by 3-4×) the capacitance of the capacitor 322. The three-port circuit element 310 is not necessarily a physical circuit element, but rather, may be a representation of a circuit element that couples the different coils to each other inductively and/or capacitively.

Figure 5:
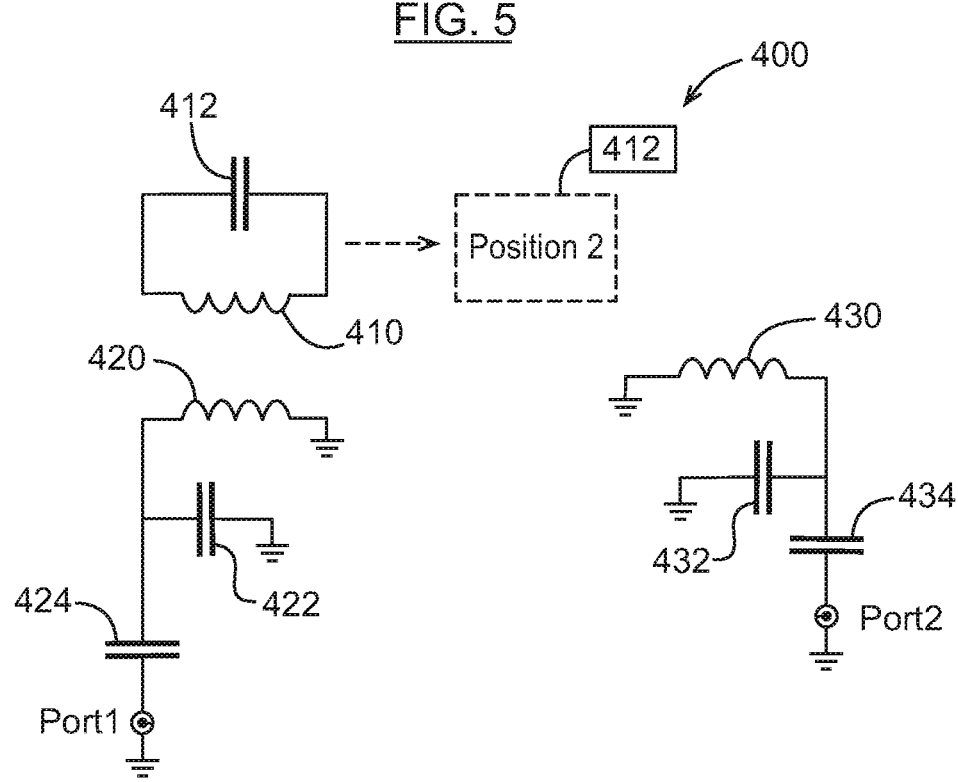
FIG. 5 is a schematic for another exemplary 3-coil continuity sensor according to one or more embodiments of the present invention.

Experimental verification of the feasibility of a 3-coil continuity sensor was further performed using a 3-coil system 400 as shown in FIG. 5. The position of the third coil 410 changes from a first position corresponding to a "closed" state to a second position corresponding to an "open" state. The fixed first and second coils 420 and 430, respectively, are shown in association with matching capacitors 422, 424, 432 and 434 for impedance matching and are resonant nominally at the same frequency. The moving third coil 410 is made resonant with a single capacitor 412 nominally at the same frequency.

When the movable coil 410 is in a first position or location corresponding to a closed continuity state, the gain between port 1 and 2 (|s21|) is small. When the movable coil 410 is in a second position or location corresponding to an open continuity state, |s21| is appreciable (e.g., significantly larger than in the first position or location), and there is a phase shift (e.g., of 180° or about 180°) close to the resonant peak. Therefore, it is possible to utilize this property to construct a continuity detector or sensor, or to measure an amount or degree of packaging/container continuity.

FIGS. 6A-F show various positions of the third coil 410 of the coil system 400 as it changes from a first position corresponding to a "closed" state in FIG. 6A to a second position corresponding to a fully "open" state in FIG. 6F. The third coil 410 is a movable coil, whereas the first coil 420 and the second coil 430 have fixed positions with respect to each other. The first, second and third coils 410, 420 and 430 are shown as concentric rings or loops, but in practice, they comprise a spiral, with a gap in each ring or loop and an electrical connection between adjacent rings or loops.

An excitation was applied at the first coil 420 when the third coil 410 in each of the positions shown in FIGS. 6A-F, measurements of the voltage on the second coil 430 were taken (using a conventional voltmeter), and plots of the voltage on the second coil 430 when the third coil 410 was in each of the positions shown in FIGS. 6A-F are shown in the corresponding FIGS. 7A-F. Thus, FIGS. 6A-F and 7A-F show or represent the signal level of a tag having 3 coils arranged as described herein as a function of the position of a cover (e.g., a hinged cover, on which the third coil 410 is placed or secured). In one example, the third coil 410 may be printed on a label that is secured to the cover using an adhesive.

The signal on the second coil 430 in FIG. 7F (corresponding to the fully "open" state of the coils in FIG. 6F) is about 4 times greater than the signal on the second coil 430 in FIG. 7A (corresponding to the "closed" state of the coils in FIG. 6A). Furthermore, the signal on the second coil 430 in FIG. 7D (corresponding to the position of the third coil 410 in FIG. 6D) is about 2 times greater than the signal on the second coil 430 in FIG. 7A. An increase in signal strength of 2× relative to the "closed" state (optionally, for at least a predetermined minimum length of time) may indicate or correspond to an "open" or "partially open" state, depending on the configuration and/or parameters of the continuity sensor (e.g., the gain of the electronic device or continuity sensor when a continuity loop therein oscillates, which must be less than the signal strength difference between "open" and "closed" states; see, e.g., the discussion of FIG. 8 below). The voltage on the second coil 430 corresponds directly to the strength of a wireless signal transmitted or broadcast by the first coil 420 and/or the extent to which the third coil 410 couples the first coil 420 to the second coil 430.

The example of FIGS. 6A-E is a relatively simple example, to verify that the concept behind the present invention is feasible. For example, the locations and/or geometries of the coils are not particularly limited and may be further optimized and/or shaped for a particular application (e.g., to conform to the product, container or packaging to which it will be applied to or into which it will be incorporated) without undue experimentation. Although a comparison of the two plots in the photos of FIGS. 7A-F show an increase of about 4× in FIG. 7F for the high-coupling state, increases in signal strength for the high-coupling (or, in this example, "opened") state of >5× relative to a low-coupling (or, in this example, "closed") state have been experimentally demonstrated. The lower plot (shown by itself in FIG. 7A) shows weak coupling (corresponding to the "closed" state shown in FIG. 6A, in which the third coil 410 is relatively far away from the second coil 430). The upper plots (especially in FIGS. 7D-F) show strong coupling, as the third coil 410 moves closer to the second coil 430. Furthermore, electrical coupling (as a dual or alternative of magnetic coupling) may be applied to, and may be more suitable for, certain situations and/or embodiments.

Non-limiting examples of articles (e.g., containers or product packaging) that have one stationary part and another part that is repeatedly movable between a first state (e.g., an open state) and a second state (e.g., a closed state) include dispensers (for example, medicine dispensers such as inhalation devices, and bottles or jars with pump dispensers), bottles or jars with caps (which may be hinged or otherwise fastened or secured to the bottle or jar), containers with hinged or sliding lids, boxes with hinged flaps such as regular slotted containers, etc.

Furthermore, as shown by the relationship between the positioning of the coils in FIGS. 6A-F and the voltages induced on the coil 430 as shown in FIGS. 7A-F, accurate sensing and/or counting can be performed as a function of the position of the passive coil 410 (e.g., the percentage of the distance between a first position corresponding to a fully closed state and a fully open state, or in the case of the passive coil 410 traversing an arcuate path, the angle of the passive coil 410 relative to the fully closed state or fully open state). For example, the "closed" state may correspond to 0-30% of the distance between the first and second positions, a "partially open" state may correspond to >30% and <80% of the distance between the first and second positions, and an "open" state may correspond to 80% or more of the distance between the first and second positions. However, the thresholds between the different continuity states can vary in different examples. The "closed" state may correspond to from 0-5% to 0-60% of the distance between the first and second positions, the "open" state may correspond to from 50% or more to 95% or more of the distance between the first and second positions, and the "partially open" or "partially closed" state may be the range of distances between the "closed" and "open" states, as long as none of the distance ranges overlap. Alternatively, the thresholds between different continuity states can be defined by the voltage induced on the second coil 430. For example, the "closed" state may correspond to a voltage of 1-1.5 times the voltage on the second coil when the passive coil is in the first position, a "partially open" state may correspond to 1.5-3 times the voltage on the second coil when the passive coil is in the first position, and an "open" state may correspond to greater than 3 times the voltage on the second coil when the passive coil is in the first position. Often, one or more inflections are apparent in the curve or plot of the voltage on the second coil as a function of the position of the passive coil, and such inflections can provide useful thresholds for determining different continuity states. The numbers given in these examples are exemplary, and the invention is not limited to these examples in any way.

FIGS. 6A to 6F will now be further described to focus on the article 481 in accordance with the invention shown therein which includes the above-described coil system 400 in accordance with the invention. It will be understood, in place of the coil system 400, this embodiment can without limitation also use an electronic device/coil system/sensor for state detection according to any of the embodiments described herein with reference to FIG. 1, FIGS. 2 to 4, FIG. 8, FIGS. 9 and 10, FIG. 11, FIG. 12 and FIG. 18 or any of those embodiments (including the specific embodiment of FIGS. 5, 6 and 7) as modified by any of (i) the disclosures made with reference to FIGS. 13 to 17 and 19, and/or (ii) the other disclosures herein, including in the 'Summary of the Invention' section and the claims.

In this embodiment, the coil system 400 is mounted to one of the outer sides 483 of the article 481 (for convenience only, termed the "front side"). The mounting of the coil system 400 to the front side 483 may be through substrates (not shown, but see the description of FIG. 2), which carry the coil system 400 and which are adhered to the external surface presented by the article's front side 483.

The article 481 in this non-limiting embodiment is the hand-held, hand-operable, breath-actuated ELLIPTA pulmonary mDPI (hereinafter the "inhaler") referred to hereinabove in the 'Discussion of the Background' section. The inhaler 481 has a mouthpiece 485 on which a user places their lips to inhale a metered dose of the medicament powder(s) in the inhaler 481. The inhaler 481 further has a mouthpiece cover 487 which has a closed position (shown in FIG. 6A) in which the cover 487 completely covers the mouthpiece 485. This defines the closed state of the inhaler 481 in which the inhaler should be kept when not in use, thereby preventing foreign objects, for example particulates, such a dust, entering the mouthpiece 485.

As shown by the sequence of FIGS. 6A to 6F, the mouthpiece cover 487 is rotatable from the closed position to an open position (shown in FIG. 6F). This movement is reversible to return the mouthpiece cover 487 from the open position to the closed position and, moreover, this back-and-forth rotation of the cover between its closed and open positions can be repeated over-and-over.

The open position of the mouthpiece cover 487 represents the open or actuated state of the inhaler 481. As described in greater detail in the International patent applications concerning the inhaler and mentioned in the 'Discussion of the Background' section, movement of the mouthpiece cover 487 from its closed position to it open position actuates the inhaler 481 by causing a metered dose of the medicament powder(s) inside the inhaler 481 to be presented at an internal airflow path in communication with the mouthpiece 485 so that a patient can thereafter inhale the dose. After the patient has inhaled the dose, the mouthpiece cover 487 is rotated back to the closed position. So, the inhaler 481 has an 'open-inhale-close' handling characteristic.

From the foregoing it will be understood that the mouthpiece cover 487 is a hand-operable actuation member of the inhaler 481. In more detail, the mouthpiece cover 487 is of an 'n'-shape (or saddle-shape) form in side view and comprises a cover section 487a at one end, which covers the mouthpiece 485 in the closed position and which a patients grips with one hand to move the mouthpiece cover 487, and a pair of spaced-apart arms (one 487b of which is partially visible in FIGS. 6B to 6F) which extend away from opposite sides of the cover section 487a to be located to the respective opposite front 483 and back (not shown) sides of the inhaler 481. These arms 487b connect the mouthpiece cover 487 to the body 489 of the inhaler 481 (which comprises inter alia the mouthpiece 485 and, therewithin, the medicament powder(s)) to a point (hidden from view) in the body 489 about which the mouthpiece cover 487 is reversibly rotatable between its closed and open positions.

In more detail, one of the arms 487b drivably connects to a rotatable component (ratchet—not shown) of the internal mechanism (a complex gear mechanism—not shown) of the inhaler 481 (which internal mechanism is located inside the body 489). The rotation of the mouthpiece cover 487 is about the axis of rotation of the ratchet and drives rotation of the ratchet therewith.

To move the inhaler 481 between its closed and open states, the patient (or other user) typically will grip the cover section 487a of the mouthpiece cover 487 in one hand and the body 489 in the other hand and then use their hands or fingers thereof to rotate the mouthpiece cover 487 relative to the body 489.

The effect of each return cycle of movement of the mouthpiece cover 487 (starting from the closed position) to the open position is a unidirectional, incremental advancement of the internal mechanism (by a ratcheting effect). The incremental advancement of the internal mechanism occurs on the opening part of the cycle, which advancement of the internal mechanism indexes the next dose of medicament powder(s) to the airflow path in communication with the mouthpiece 485 (unless no doses are left or present). On the closing part of the cycle, the ratchet is reset ready for the next cycle.

A subtlety of the opening part of the cycle of the mouthpiece cover 487 is that there is no drive from the mouthpiece cover to the internal mechanism in the initial phase of the opening movement of the mouthpiece cover 487 from its closed position, as is described in detail in WO2007/012871. This 'lost-motion' occurs until the mouthpiece cover 487 has moved to a position (see FIG. 6B) in which the mouthpiece 485 is partially opened, whereupon the drive from the mouthpiece cover 487 to the internal mechanism engages (the rotating ratchet engages a ratchet gear) and stays engaged for the rest of the opening movement of the mouthpiece cover to the open position (i.e. from the mouthpiece cover position of FIG. 6B to its fully open position in FIG. 6F). The lost-motion allows for intentional partial opening of the mouthpiece cover 487 for cleaning of the mouthpiece 485, as well as inadvertent/intentional play of the mouthpiece cover 487 when in its closed position, between successive inhaler uses, without resulting in indexing or partial indexing of a new dose of the medicament powder(s).

The unidirectional, incremental advancement of the internal mechanism caused by each opening of the mouthpiece cover 487 also results in a dose counter, visible through a window on the front side 483 of the inhaler body 489 (not shown), to be decremented until the end of the dose count. The dose count indicates the number of doses of the medicament powder(s) remaining in the inhaler.

As can be seen from FIGS. 6A to 6F, the coil system 400 is mounted to the front side 483 of the inhaler 481 such that the coil 410 is on the mouthpiece cover 487 and that the coils 420, 430 (which may be referred to as a driver coil and a detector coil) are on the inhaler body 489 in fixed positions. In this way, the coil system 400 is able to detect which state (closed or open/actuated) the inhaler is in by detecting whether the mouthpiece cover 487 is in its closed or open position.

Based on the operation of the ELLIPTA inhaler, the coil system 400 can form a compliance (or adherence) monitor for the inhaler 481 inasmuch as the detection of the open state of the inhaler is a surrogate for a dose being delivered to a patient; i.e. if the inhaler has been moved from its closed state to its open state, by moving the mouthpiece cover 487 from its closed position to its open position, this indicates that the metered dose indexed to the airflow path will be inhaled by a user before the inhaler 481 is (re)closed.

As will be known, a patient will need to take a metered dose of the medicament powder(s) in the inhaler 481 according to a prescribed dosing regimen, for instance once-a-day. Thus, compliance (or adherence) of a patient to that prescribed dosing regimen may be assessed by comparing the prescribed dosing interval (e.g. 24 hours for once-daily-dosing) to the periods of elapsed time between each opening event of the inhaler 481 detected by the coil system 400. Clearly, such compliance information will be useful to observe relationships between clinical outcomes with compliance behaviour, both in clinical trials and real-world settings.

As mentioned in the 'Discussion of the Background' section, while the proper use of the ELLIPTA inhaler 481 is movement of the mouthpiece cover 487 between its full stroke positions (FIG. 6A and FIG. 6F), it will work correctly if the mouthpiece cover 487 moves back-and-forth to at least predetermined positions short of these full stroke positions. So, for instance, for the inhaler 481 to be closed properly the mouthpiece cover 487 has to be closed sufficiently far enough for the ratchet to reset (e.g. corresponding to the mouthpiece cover position shown in FIG. 6B), otherwise the subsequent opening event will not index the next metered dose. For the inhaler 481 to be opened correctly, the mouthpiece cover 487 has to be opened from a closed position, i.e. closed fully or to at least the predetermined position indicated above, to a point sufficiently far that the indexing makes the next metered dose of powder(s) available for inhalation (e.g. corresponding to the mouthpiece cover position shown in FIG. 6E).

The coil system 400 may therefore be arranged to detect the full stroke positions (or very close approximations thereto) so that anything less than full opening or full closing represents a misuse of the inhaler. Alternatively, the coil system 400 may be arranged to detect open and closed states as based on the mouthpiece cover being moved to at least the predetermined positions when moving in the opening or closing direction. A misuse event can therefore be detected by the coil system 400 as the mouthpiece cover not been moved sufficiently far in one direction and/or the other during a use event cycle for the inhaler 481 to have been operated correctly. Another potential alternative is for the coil system 400 to detect and discriminate both positions for extra data on the usage (proper vs acceptable); e.g. for training purposes.

Consequently, the coil system 400 can also provide information not just on whether the ELLIPTA inhaler has been used, which can be used for compliance monitoring, but also on whether such use is proper/acceptable or not.

So, in the context of the invention an article's state means that the article is in that state on an absolute basis (like the fully open/closed state of the inhaler 481) and/or is deemed to be in that state (like the inhaler 481 being deemed in its open or closed states if the mouthpiece cover 487 has moved to at least predetermined opening/closing positions). In the latter instance, what is deemed to be the state of concern (i.e. to be sensed) will depend on the article at issue, but this is well within the normal practice of the skilled person in the art.

While in the above-described inhaler the coil system 400 is mounted to the external surface of the inhaler front side 483, it may be mounted to the external surface of the opposite rear side of the inhaler (not shown). Further alternatively, embodiments can be envisioned in which the coil system 400 is mounted to an inner surface of the inhaler 481. In addition, a variety of different means can be envisioned for the inhaler 481 to carry the coil system 400, such as having the coil system 400 integrated into the inhaler 481, as for example by embedding into the inhaler's physical structure (e.g. by integrating into the physical structure of the mouthpiece cover 487 and the body 489).

The above-described inhaler embodiment establishes that the invention has utility for articles of the type having a plurality of (e.g. two or more) different states (e.g. open and closed; actuated/primed/operated and rest/return; etc.) to detect one, more or all of those states the article is in. Such utility is present for a single-use article (e.g. open or actuate only once), but more especially for a reusable or multi-use article (e.g. one that is repeatedly openable or actuatable by moving (e.g. reversibly or reciprocally) between its different states).

Of course, the invention has a particular utility for those articles whose usage it is desirable to monitor or detect, such as articles with a prescribed usage regimen. As an example, mention may be made of healthcare products which have a prescribed usage or dosing regime, including pharmaceutical dispensers (injectors, inhalers, etc.) for dispensing a pharmaceutical to a prescribed dosing regimen.

As with the inhaler 481 described above, such articles will typically be moved from one state to another through the relative movement of two article structures between different positions, for instance by relative movement of two article parts (e.g. a closure (cover or cap), on the one hand, and a body, on the other hand). The coil system 400 may then be arranged so that the coil 410 is located on one structure and the coils 420, 430 are located on the other structure (e.g. in fixed positions) such that the respective positions of the coils in the different relative positions of those structures results in differentiable coil coupling of the coils 420, 430 with the coil 410 for detection of the different states. Of course, the other types of electronic devices/coil systems/sensors disclosed herein may be similarly arranged on such articles to the same effect.

Figure 8:
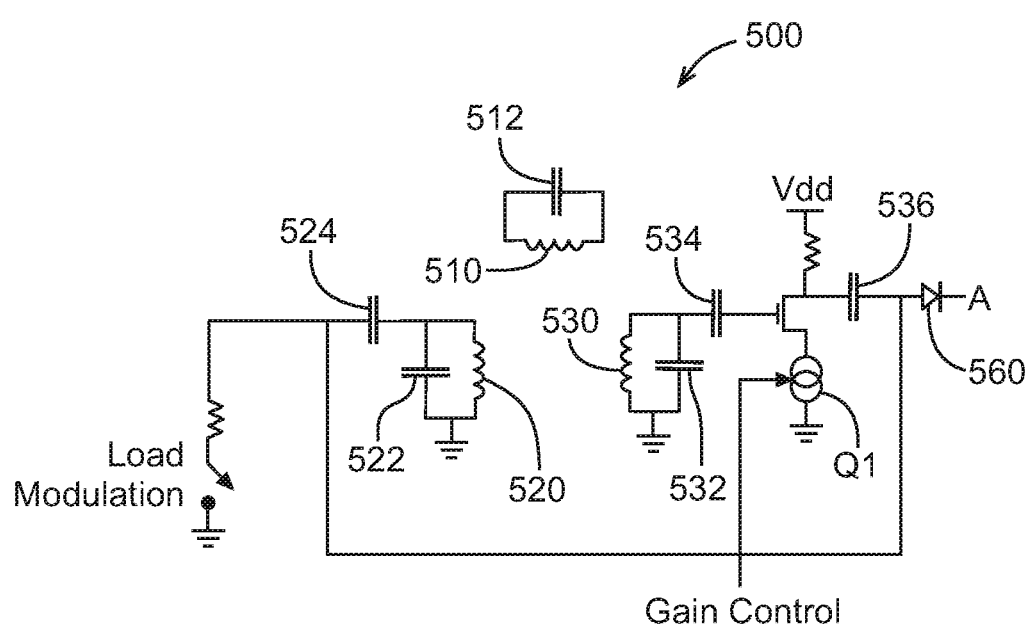
FIG. 8 is a schematic for yet another exemplary 3-coil continuity sensor according to one or more embodiments of the present invention.

FIG. 8 shows another equivalent circuit for an exemplary continuity sensor in accordance with one or more embodiments of the present invention. The above-described properties of the three-coil system can be used to induce positive feedback resulting in oscillation. In one embodiment, the combination of three coils (e.g., the first, third and second coils) is placed in the feedback path of an amplifier to induce oscillations.

Gain control in the transistor Q1 is achieved by changing a bias current at the gate of the transistor Q1, which is controlled by the amount of coupling of an excitation at the first coil 520 to the second coil 530, and/or by applying a bias current to a source/drain terminal of the transistor Q. The bias current (e.g., source/drain current) is under open loop control, which is advantageous for embodiments in which the sensor and IC are powered by a battery, as open loop control (e.g., without use of feedback) conserves battery power when the high-coupling state is maintained for a relatively long period of time, and helps with NFC and possibly other wireless communications while the sensor is in the high-coupling state. By default, the gain of the transistor Q1 is set to a low enough value that current drain is small. This is particularly advantageous in embodiments in which the tag/electronic device is powered by a battery, rather than by extraction of power from a received wireless (e.g., RF or NFC) signal (which is the case in some alternative embodiments). Also, in one or more embodiments, the Load Modulation switch is off.

In a weak coupling scenario, there may not be enough loop gain in the transistor Q1 to overcome losses in the coils 510, 530 and 550 and induce oscillations (e.g., in a loop comprising the first, third and second coils 510, 530 and 550 and the transistor Q1). For example, when the third coil 510 is absent or far away (e.g., from the second coil 550), losses in the coils 510, 530 and 550 increase or are relatively high, which can bring the loop gain to below unity (e.g., <1). In this condition, oscillations may not occur. However, when the third coil 510 is in a position to introduce strong coupling, the loop gain can exceed unity, and the loop phase shift is 0° (e.g., since the first, third and second coils 510, 530 and 550 introduce a 180° phase shift near resonance, as does the transistor Q1, resulting in a total phase shift of 0° in the loop). The oscillations, which occur when the continuity state of a container or product packaging on which the electronic device is attached or secured is a high-coupling state, generate a DC voltage at the output A of the diode 560. The amplitude of the oscillations (e.g., the amount of coupling) determines the magnitude of the DC voltage at output A of the diode 560.

The electrical device 500 may be used for wireless (e.g., NFC or RF) read operations. The antenna(s) 510, 520 and 530 as described above are used to sense the presence of an NFC signal from a handheld device (such as an NFC-enabled smart phone) and communicate back to the handheld device. In presence of an NFC field, a finite voltage gets generated at the output A of the diode 560 even in the "closed" (e.g., weak coupling) state (i.e., where there is no oscillation). However, the diode 560 detects the oscillations when the voltage at output A has a duration that exceeds a predetermined threshold (e.g., a duration that is longer or significantly longer than that caused by NFC or other wireless interrogation). However, there may be other components and/or ways to detect the oscillation, so the invention is not limited to use of a diode to do so. The load modulation switch may be activated when the voltage at the diode output A exceeds a threshold voltage.

Thus, the voltage at the diode output A representing the continuity state of a container or product packaging on which the electronic device is attached or secured can be differentiated by observing, monitoring and/or measuring the duration of the voltage at the diode output A. Other techniques for differentiating between the continuity sensor output and the wireless (e.g., RF or NFC) field include amplitude modulation (e.g., detection of a signal having a different amplitude), frequency modulation (e.g., detection of a signal having a different frequency), switching (e.g., the diode output A, which may be connected to an NFC communication circuit under normal operation, may be periodically disconnected from the NFC communication circuit and temporarily connected to the sensor while the first [red] coil 510 is being driven), and relative measurement (e.g., detecting the rising edge that occurs when the first [red] coil 510 is initially driven). Whereas the NFC interrogation may be few seconds at most, the "open" state of the container or product packaging generally lasts longer than the NFC interrogation (e.g., frequently for at least tens of seconds, and in some cases, permanently). Usually, the occurrence of an NFC interrogation and the opening of the container or product packaging do not occur simultaneously, and are thus assumed to be separate or mutually exclusive events.

If the handheld device is brought in proximity to the electronic device and/or continuity sensor during the time that oscillation occurs in the coil-transistor loop due to an "open" continuity state, there will be a collision between electromagnetic signals (e.g., in the coil-transistor loop), and the NFC interrogation will fail. To mitigate this scenario (and conserve battery power in embodiments including a battery), the gain control signal is not a DC signal, but rather, a sequence of pulses having a predetermined duty-cycle. The duty cycle (e.g., 50% on, 50% off in each cycle) provides time intervals when the oscillation in the loop stops. During these intervals, an NFC interrogation can succeed.

In an alternative embodiment, the above-described properties of the three-coil system can be used to induce positive feedback resulting in a change in state of the bistable electronic device. In addition, the present continuity sensor can work in a complementary fashion (i.e., the closed state may correspond to relatively strong coupling and a relatively strong signal [i.e., a "high-coupling state"], and the "open" state may correspond to relatively weak coupling and a relatively a weak signal [i.e., a "low-coupling state"]). However, in oscillation-based embodiments of the electronic device that include a battery, such a complementary continuity sensor may cause a constant current drain from the battery. Thus, the complementary continuity sensor may be more suitable for a bistable sensors in electronic devices that extract power from a received wireless signal (e.g., in which one coil/antenna is coupled to an integrated circuit that includes a rectifier).

Figure 9:
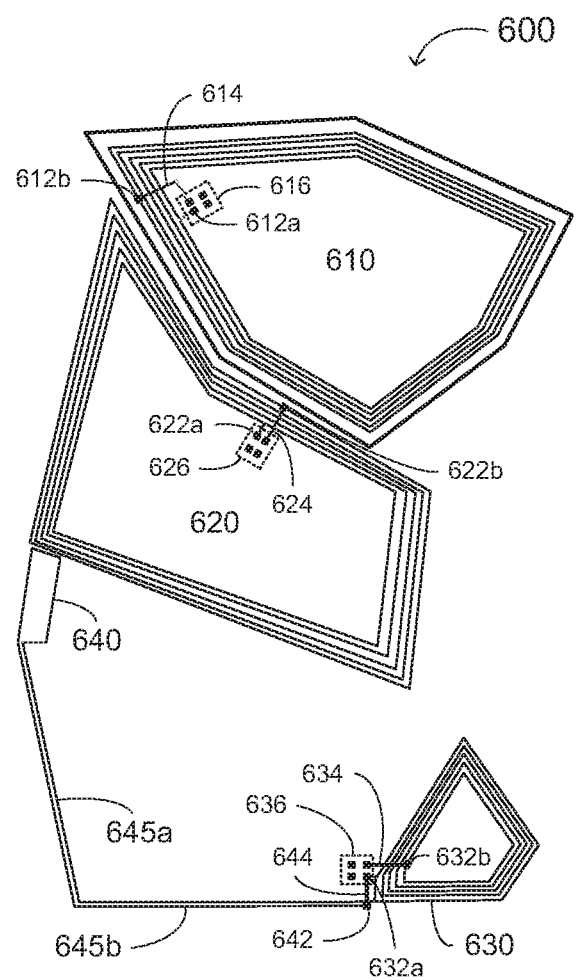
FIG. 9 shows an exemplary four-coil continuity sensing system according to one or more embodiments of the present invention, in which an auxiliary coil is added to the present three-coil system.

FIG. 9 shows an exemplary four-coil continuity sensing system 600 according to one or more embodiments of the present invention, in which an auxiliary (or compensation) coil 640 is added to a three-coil system comprising moving coil 610 and stationary coils 620 and 630. Each of the moving coil 610 and stationary coils 620 and 630 includes first and second terminals 612*a-b*, 622*a-b* and 632*a-b*, respectively, configured for electrical attachment (directly or indirectly) to an IC (not shown). The coils 610, 620 and 630 are connected to an IC and/or discrete component (such as a capacitor) through bond pads 616, 626 and 636, respectively. The second (outer) terminals 612*b*, 622*b* and 632*b* are electrically connected to one of the bond pads 616, 626 and 636 (other than the first terminal 612*a*, 622*a* and 632*a*) by a strap 614, 624 and 634, respectively. Typically, the straps 614, 624 and 634 are isolated from the coils 610, 620 and 630 by an insulation layer, which may comprise a plastic, a glass, ceramic or other electrical insulator. The bond pads 616, 626 and 636 other than those connected to a coil 610, 620 or 630 may be connected to traces that electrically connect one or more other components, such as a battery, an external sensor, one or more resistors and/or capacitors, a display, etc. to the IC. The first terminals 612a, 622a and 632a and the bond pads connected to the second terminals 612b, 622b and 632b may also be connected to one or more traces that electrically connect another component to the IC.

The auxiliary loop 640 is configured to reduce a low residual coupling that may be present between the second stationary coil 630 and the first stationary coil 620, and may further compensate for the impedance of the second stationary coil 630. The auxiliary loop 640 may have dimensions and/or a number of loops sufficient to provide a predetermined or desired amount of impedance compensation. The auxiliary loop 640 is connected to the second stationary coil 630 by a first trace 645a and to an IC (not shown) by a second trace 645b, a terminal 642, and a strap 644 (which is isolated from the first and second traces 645a-b by an insulator, as described herein). In the absence of the auxiliary coil 640, there may be some unintentional coupling between the first and second stationary coils 420 and 430. The unintentional coupling tends to reduce the sensitivity (e.g., of the first and second stationary coils 420 and 430) to the presence of the moving coil 410, and the moving coil 410 has to first overcome any unintentional coupling to create a significant change in the second stationary coil 430. The auxiliary loop 640 may reduce this unintentional coupling, and consequently enhance sensitivity of the system to the presence of the moving coil 410 as it approaches the second stationary coil 430.

Figure 10A:
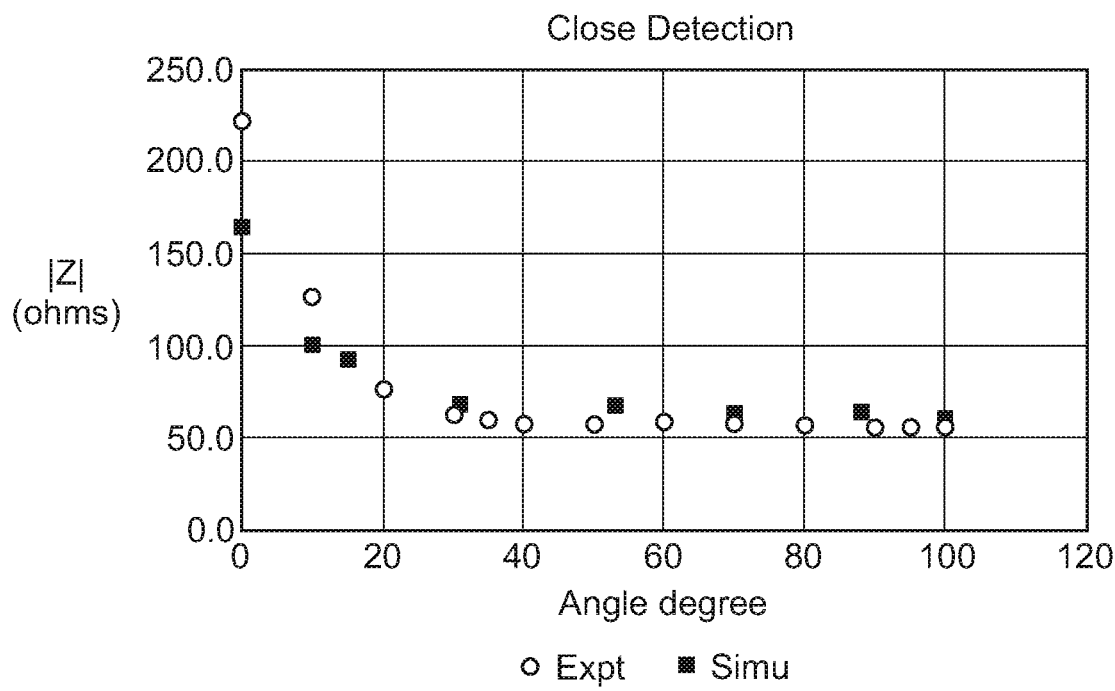
FIGS. 10A-B show results for the exemplary four-coil continuity sensing system of FIG. 9, in accordance with one or more embodiments of the present invention.

FIG. 10A is a graph showing the correlation between experiment and simulation for detection of a closed state in an example of the present continuity sensor containing the 3-coil system 410, 420 and 430 and the auxiliary coil 640 in FIG. 9, secured to a product container having a cap or lid that opens angularly (i.e., by pivoting on a spindle, rod or other connection between the cap/lid and the body of the container), such as the ELLIPTA inhaler shown in FIGS. 6A to 6F. The plotted data show the impedance (in ohms) of the first stationary coil 420 as a function of the angle of the moving coil 410 relative to the first stationary coil 420. The effect of the auxiliary coil 640 is always present.

Figure 10B:
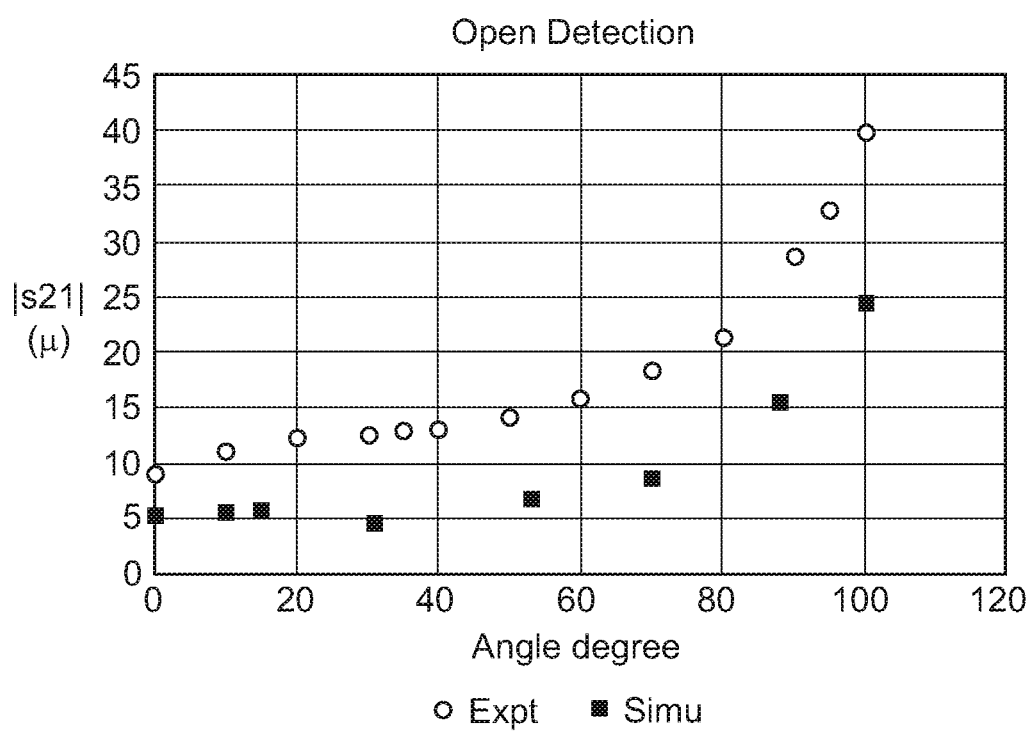

FIG. 10B shows the gain between port 1 and port 2 (see, e.g., FIG. 5) for open-state detection of the same system as that for which the test results in FIG. 10A were obtained. FIG. 10B shows increased coupling (e.g., between the first and second stationary coils 420 and 430) as a function of the angle of the moving coil 410 relative to the first stationary coil 420. The effect of the auxiliary coil 640 is always present.

There is no change in permeability as the angle of the moving coil 410 relative to the first stationary coil 420 changes, or during closed-state vs. open-state detection. No ferro- or ferrimagnetic material is present. In the open state, the moving coil 410 couples an oscillating signal from the first stationary coil 420 to the second stationary coil 430, resulting in a signal on the second stationary coil 430 sufficiently strong to generate an "open state" flag. During the closed state, the moving coil 410 loads the first stationary coil 420 sufficiently to reduce the effective impedance seen by a transistor providing a bias to the output of the first stationary coil 420 (e.g., transistor 742 in FIG. 11), resulting in a reduced RF voltage at the drain of the transistor. This way, the sensitivity to the angle (or distance) variation between the moving coil 410 and the first stationary coil 420 around the thresholds for detecting the closed and open states can be achieved.

The use of an auxiliary coil is not limited to the particular embodiment herein described, but may be deployed in other embodiments as will be understood by the skilled person in the art.

Figure 11:
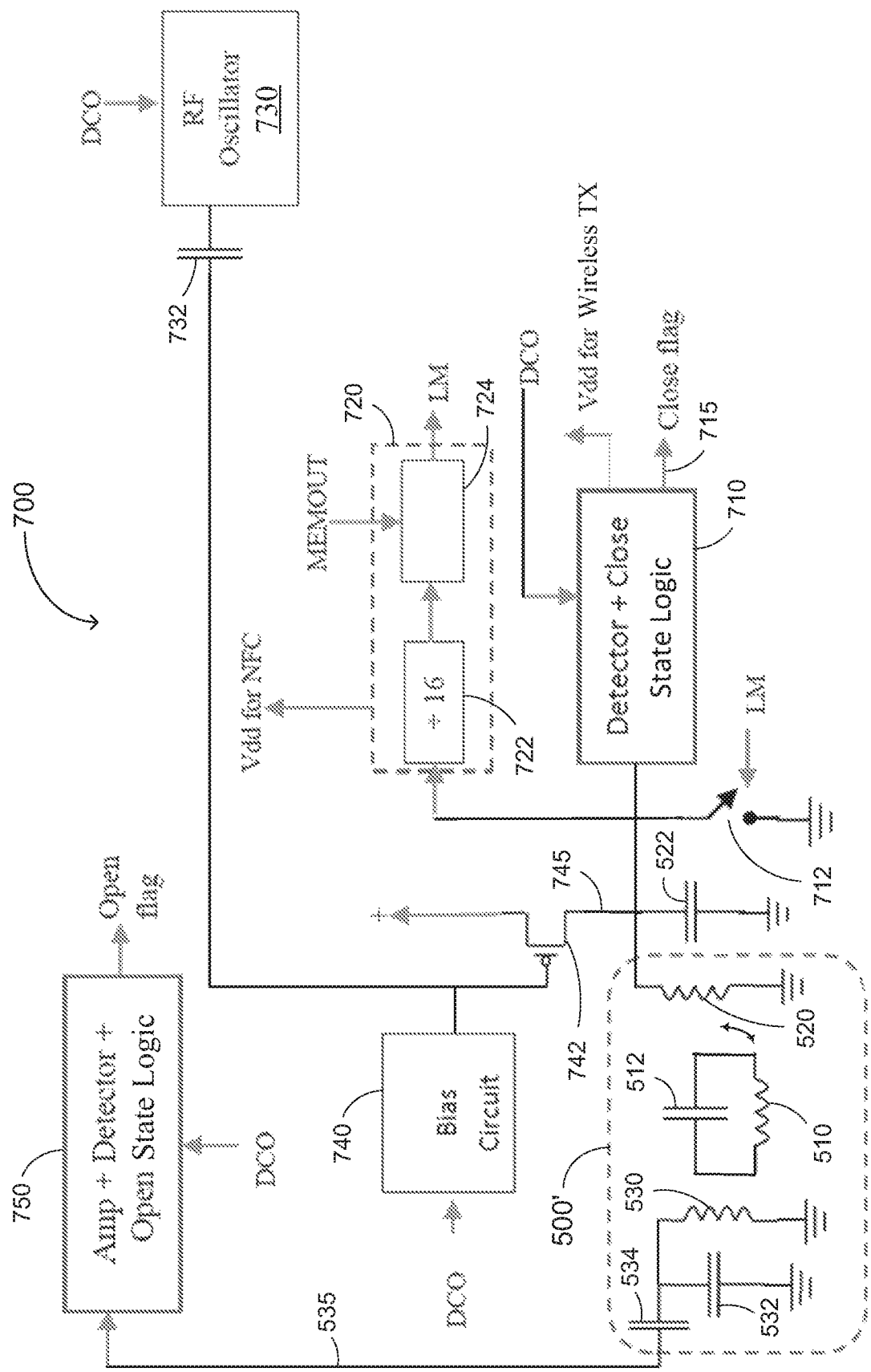
FIG. 11 shows an exemplary integrated circuit for use with an exemplary three-coil continuity sensor according to one or more embodiments of the present invention.

FIG. 11 shows an exemplary integrated circuit (IC) 700 for use in conjunction with a further example of the present 3-coil continuity detector 500'. Similar to the continuity detector 500 in FIG. 8, the continuity detector 500' includes a first moving coil 510, a first capacitor 512 connected to a terminal of the first coil 510, a second "closed state" coil 520, a second capacitor 522 (which may be part of the integrated circuit 700) connected to a terminal of second coil 520, a third "open state" coil 530, and third and fourth capacitors 532 and 534 connected to a terminal of the third coil 530. The first coil 510 moves between the position shown, which corresponds in this example to an open state of the container or packaging, and a position rotated counterclockwise from about 60° to about 120° (and in one example, about) 90-100°, corresponding to a closed state of the container or packaging. Alternatively, the first coil 510 may moves between the position shown and a position parallel or substantially parallel with the second coil 520.

The IC 700 includes a first continuity state detector and closed state logic 710, load modulation logic 720, an RF oscillator 730, a bias circuit 740, and an amplifier, second continuity state detector and open state logic 750. The first continuity state detector and closed state logic 710 receives an output signal from the second coil 520, an output signal from a load modulation switch 712, and a periodic (e.g., clock) signal from a digitally-controlled oscillator (DCO; not shown). A bias 745 is also applied to the first continuity state detector and closed state logic 710 by the bias circuit 740 and a transistor 742. The periodic signal from the DCO is also received by the RF oscillator 730 and the amplifier, second continuity state detector and open state logic 750.

During operation of the IC 700, the transistor 742 is biased in saturation mode by the DCO, the output of which is received by the bias circuit 740. The DCO may also be a low power oscillator (LPO). Otherwise, the transistor 742 is turned off by the DCO. The signal output signal from the second coil 520 (biased by the bias circuit 740 and transistor 742), is modulated (e.g., has its amplitude reduced) when the load modulation switch 712 is closed. The load modulation switch 712 is closed and opened by the output of the load modulation logic 720.

In the closed state, the first coil 510 is rotated towards the second coil 520, and the signal output from the second coil 520 is relatively high. Thus, the detector and logic in the first continuity state detector and closed state logic 710 may comprise a threshold detector that outputs an active "closed state" flag 715. In addition, the first continuity state detector and closed state logic 710 may output a signal ("Vdd for Wireless TX") to wireless communication circuitry, such as a modulator (see, e.g., FIG. 19), for wireless transmission to an external receiver. The signal may comprise a power supply or a data signal, and the wireless communication circuitry may output an amplitude-modulated signal.

In the open state, the first coil 510 couples the signal from the second coil 520 to the third coil 530, resulting in an output signal 535 having sufficient strength to generate an "open state" flag from the amplifier, second continuity state detector and open state logic 750. During the closed state, the first coil 510 loads the second coil 520 sufficiently to reduce the effective impedance seen by transistor 742, resulting in a reduced RF voltage at the drain of transistor 742. This creates the "closed state" flag 715. In this manner, the continuity sensor 500 may have increased sensitivity to variations in the angle between the first coil 510 and the second and/or third coils 520 and/or 530 around the thresholds for the closed and open states (and, when there is a gap between the thresholds for the closed and open states with no overlap between the closed and open states, the thresholds for a "partially closed" or "partially open" state between the closed and open states).

In some embodiments, each of the stationary coils is associated with an independent integrated circuit (IC). For example, a first IC is electrically connected to the first stationary coil, and a separate second IC is electrically connected to the second. stationary coil. Each of the first and second ICs may be a printed IC (PIC). In the example of FIG. 11, the first IC is electrically connected to the second coil 520, and the second IC is electrically connected to the third coil 530.

Generally, the first and second ICs may include an oscillator (e.g., a low power oscillator), an open or closed state sensor and/or detector, and a controller (a microcontroller or control logic circuit). One or both of the first and second ICs may include a memory (e.g., a non-volatile or one-time programmable [OTP] memory comprising a plurality of memory cells or elements) and a memory write (or programming) circuit. The first and second ICs may have the same or a different configuration.

In further embodiments, the second IC (connected to the second stationary coil 530) may include a real-time sensor or timer circuit, a memory and a controller configured to (i) record the time at which the device was opened and (ii) determine if a sample of the product was taken or the device was actually used each time that the container or package was opened. In one example, the controller determines if a sample was taken or the device was used through an app (e.g., on a programmed NFC reader, such as a smart phone) that reads the memory (or the part thereof) that stores the continuity sensor output (e.g., using an NFC protocol).

Figure 12A:
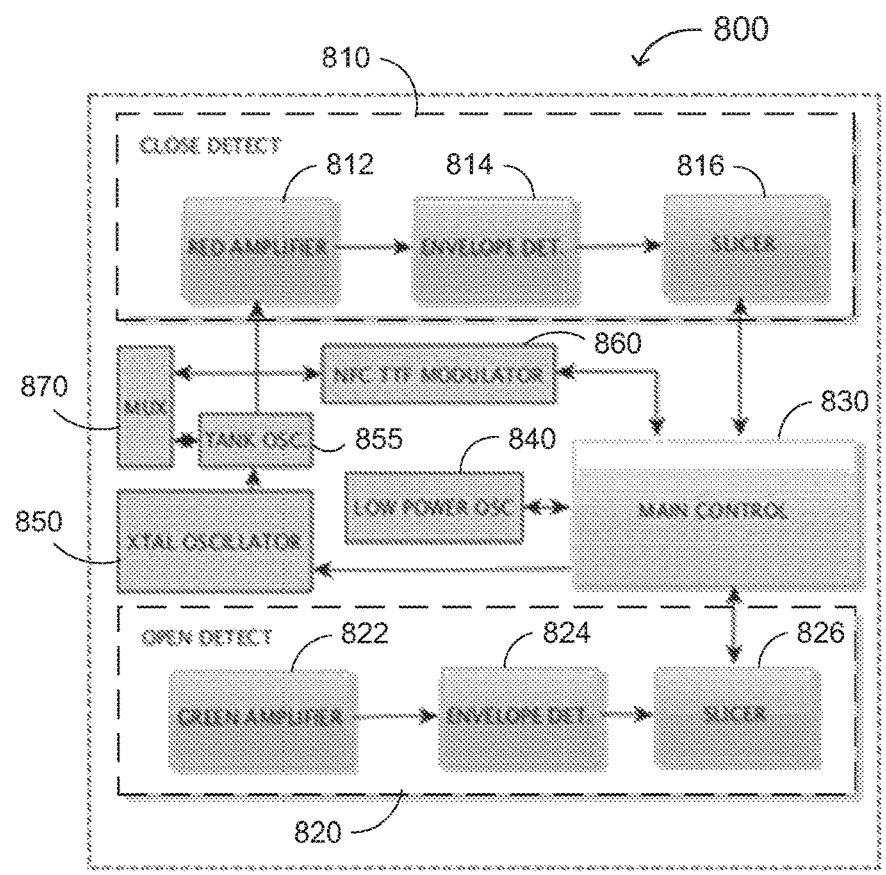
FIGS. 12A-B show exemplary alternative integrated circuitry to be connected to the first and second stationary coils of the present continuity sensor according to one or more embodiments of the present invention.
Figure 12B:
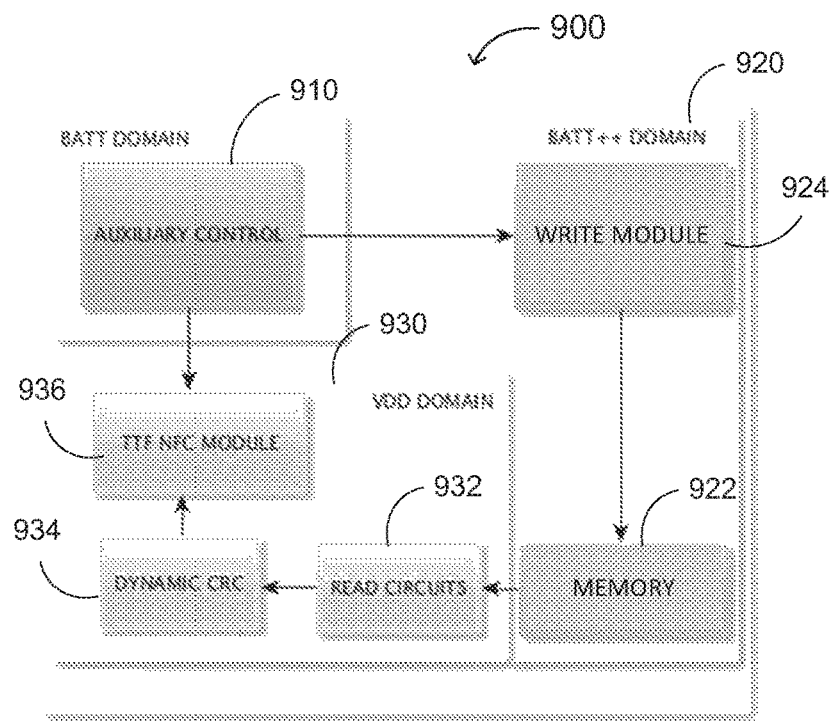

FIGS. 12A-B show an alternative solution for the integrated circuitry to be connected to the first and second stationary coils. FIG. 12A shows a first printed IC (PIC) 800, and FIG. 12B shows a second PIC 900. One or both of the first and second PICs 800 and 900 may be manufactured by printing a doped polysilane (PDPS) ink to form semiconducting features or structures in the PIC.

Referring to FIG. 12A, PIC 800 contains open and closed state sensor/detector blocks 810 and 820, a main controller 830, a low power oscillator 840 configured to help the controller 830 manage power and count time slots (e.g., points in time when the container or package is opened), and a wireless (e.g., NFC) modulator 860. The MCU 830 can also control memory read and write operations and frame or information packet generation. The controller 830 also interfaces with a controller on the second PIC 900, which manages write and read operations of all memories, dynamically generates error codes (e.g., cyclic redundancy check [CRC] code), assembles the frame or information packet to be transmitted wirelessly, and serially transmit the frame or information packet to the NFC modulator 860 in the first PIC 800, which then communicates wirelessly with the reader (not shown).

The first PIC 800 may perform any of a number of tasks. For example, the first PIC 800 may assist the first stationary ("red") coil to perform its role in the three-antenna sensor system (e.g., system 400 in FIG. 5 or system 500 in FIG. 8) and communicate wirelessly with a scanner and/or reader. A crystal oscillator 850 on the first PIC 800 may energize the first stationary coil (or antenna) during the "closed state" detection mode or process, and can provide a link from the wireless reader to the sensor system using a wireless protocol in the memory read mode (e.g., during a memory read operation).

During closed state detection, the degree or extent of coupling between the first stationary coil and the moving ("blue") coil or antenna changes the load impedance of the amplifier 812 receiving the output of the first stationary coil that is amplified by the amplifier 812 and detected by the closed state envelope detector 814. This is shown in the closed state detector block/module 810. Similarly, during open state detection, the degree or extent of coupling between the first stationary coil and second stationary ("green") coil or antenna via the moving coil is amplified by the amplifier 822 receiving the output of the second stationary coil and detected by the open state envelope detector 824. This is shown in the open state detector block/module 820. The amplifier gains are directly proportional to the respective impedances, and the peak voltage swings are detected by the respective closed and open state envelope detectors 814 and 824. The DC voltages from the envelope detectors 814 and 824 are compared against one or more pre-set reference by the slicers 816 and 826, respectively, to generate the signal output by the slicers 816 and 826.

The first PIC 800 may read an incoming wireless (e.g., NFC) frame from the second PIC 900. For example, the memory 922 (FIG. 12B) may store an intended or prescribed usage pattern (e.g., a drug dose delivery regimen or schedule). When a memory read operation is initiated by a wireless reader such as a smartphone, the read mode is detected, and the MCU 830 signals the auxiliary controller 910 on the second PIC 900 to read the memory 922. Error checking code (e.g., CRC) is added to the data from the memory 922 by error code block 934, and the serial data from the second PIC 900 is then encoded and modulated by the encoding module 936 (e.g., as per an NFC protocol). The encoding module 936 may also encode and modulate the serial data from the second PIC 900 according to a second wireless protocol, such as a "tags-talk-first" (TTF) protocol.

The first PIC 800 may include the main controller 830 for the overall continuity sensing system, and may interface with the auxiliary controller 910 of the second PIC 900. The first PIC 800 may provide power management for the continuity sensing system using a low power oscillator 840 to power various blocks during different cycles or operations. The first PIC 800 may also perform a time keeping function by providing one or more timing signals (e.g., a real-time signal, with a frequency of, e.g., 1 Hz) to the second PIC 900, which manages (e.g., records and reads out) time slots using the memory write module 924, the memory 922, and the memory read circuitry 932.

The parameters of the low power oscillator 840 may be determined from the capacity of the battery (not shown) after self-discharge, the standby leakage current for the entire continuity sensing system, the power consumption when the continuity sensing system is active, the duration of time during which the continuity sensing system is in a standby state and is active (e.g., for an expected period of use, such as one month, 60 days, 90 days, 1 year, etc.), and the duty cycle (e.g., the ratio of active operation time to standby time).

In various embodiments, the oscillator variation over temperature, battery drop (e.g., output voltage decrease over time) and aging is within 1.0% or less (e.g., within 0.6%, 0.4%, etc.) to minimize or control a total error (e.g., in the real-time clock function). When the operating frequency is below a certain threshold, trimming the oscillator (e.g., coupling the oscillator signal or a bias to the oscillator with one or more resistors and/or capacitors) to a relatively high accuracy (e.g., 0.25%) may be challenging and may consume more area than is desired. Operating the oscillator 840 at a higher frequency (e.g., above the certain threshold) reduces the challenge of trimming and facilitates generating a duty cycle appropriate for power cycling (for example, when the time of active operation is in a range of 0.1-100 ms and the oscillator frequency is in a range of 0.1-1000 Hz [e.g., 1 Hz]). However, operating the oscillator 840 at a higher frequency may increase the dynamic power consumption.

Figure 13A:
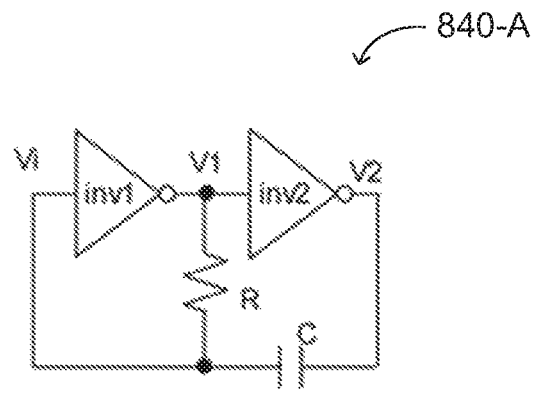
FIGS. 13A-C show circuit diagrams of exemplary oscillators for use with and/or in the exemplary integrated circuitry connected to the present continuity sensor according to one or more embodiments of the present invention.

FIG. 13A shows a circuit diagram of a relatively simple two-inverter RC oscillator 840-A suitable for use as the low power oscillator 840 in the IC 800 of FIG. 12A. The RC oscillator 840-A includes a first inverter inv1, a second inverter inv2, a capacitor C in series with the first and second inverters inv1 and inv2, and a resistor R connected to (i) the node V1 between the first and second inverters inv1 and inv2 and (ii) a node Vi (e.g., the input to the first inverter inv1 and/or a terminal or electrode of the capacitor C). The other terminal or electrode of the capacitor C is connected to the output V2 of the second inverter inv2.

The two-inverter RC oscillator 840-A can generate a periodic signal with a relatively low frequency (e.g., in the range of 0.1 Hz-1.0 kHz) using the resistor R and the capacitor C. The period (i.e., the reciprocal of the frequency) of the oscillator 840-A can be calculated according to Equation [1]:

$$\text{Oscillator Period} = RC \cdot \ln\frac{V_T + V_{DD}}{V_T} + RC \cdot \ln\frac{V_T - 2V_{DD}}{V_T - V_{DD}} \quad [1]$$

where $V_{DD}$ is power supply voltage to the oscillator, $V_T$ is the threshold voltage at which the inverters inv1 and inv2 switch output states, R is the resistance of resistor R, and C is the capacitance of capacitor C.

The frequency of the oscillator 840-A is directly proportional to R and C. The reduce power consumption and generate a periodic signal having a relatively low frequency (e.g., on the order of 0.1-10 Hz) using the oscillator 840-A, the resistor R and the capacitor C may be external to the integrated circuit 800 (FIG. 12A) to create a large time constant. Placing the resistor R and the capacitor C on the substrate or die of the integrated circuit 800 may cause the integrated circuit 800 to have a larger area than desired (e.g., for the dimensions and/or aesthetics of the product packaging). The accuracy of the oscillator 840-A may be controlled by the tolerances of the resistor R and the capacitor C, which may be less challenging when they are external to the integrated circuit 800. The frequency of the oscillator 840-A is dependent on the ratio $V_T/V_{DD}$, which may be trimmed in the integrated circuit 800. This ratio changes as a function of supply voltage (i.e., $V_{DD}$), as the switching threshold of the inverters inv1 and inv2 does not scale or change with changes in $V_{DD}$. To trim the frequency of the oscillator 840-A, a capacitor bank may be included in parallel with the capacitor C, and one or more of the capacitors in the capacitor bank may be included in the circuit 840-A (e.g., using one or more switches connected to the capacitors in the capacitor bank) to produce a particular and/or desired frequency at a particular supply voltage.

A possible disadvantage of the oscillator 840-A is that its charging and discharging currents may vary with the supply voltage. Accordingly, the oscillator 840-A may consume greater power as the supply voltage increases. External resistor and capacitor components may also make the oscillator 840-A relatively susceptible to electrostatic discharge (ESD) damage.

As the battery voltage drops, the frequency of the oscillator 840 (FIG. 12A) is affected. The frequency variation of the oscillator 840 can be mitigated by operating the oscillator at a fixed voltage that stays relatively constant as the battery drops, and can be controlled by regulating its supply voltage using a voltage regulator (e.g., a low-power, low-drop out regulator). The voltage regulator may provide a relatively constant DC voltage output (optionally at predetermined maximum load current, for example of 1-100 μA). A conventional low-power reference voltage generator (which may receive a supply voltage from the battery) may be external to the IC 800.

Figure 14A:
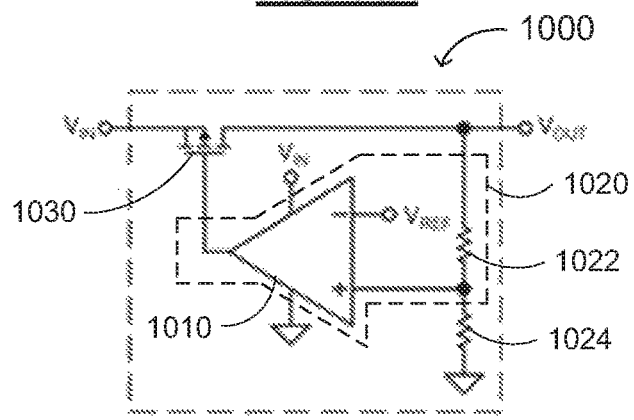
FIGS. 14A-B show circuit diagrams of exemplary voltage regulators suitable for use with the present continuity sensors, in accordance with one or more embodiments of the present invention.

FIG. 14A shows a circuit diagram of a single-stage, low-dropout regulator 1000 that generates a relatively constant, fixed voltage at node $V_{OUT}$ as the battery drops. The regulator 1000 comprises a fixed-current operational amplifier (OP-AMP) 1010 in a feedback loop 1020 that controls a p-channel transistor 1030. The regulator 1000 is configured to regulate a predetermined output voltage ($V_{OUT}$) of, e.g., 1.5-3.3V. The output $V_{OUT}$ of the regulator 1000 decreases logarithmically with increasing DC load current. However, in an embodiment configured to regulated to an output voltage of 2.5V, the output $V_{OUT}$ of the regulator 1000 was within ±0.1V over a DC load current from 10% of the maximum load current to the maximum load current.

Power consumption by the regulator 1000 may be reduced or minimized by keeping the bandwidth of the regulator 1000 relatively low (<100 kHz, <10 kHz, <1 kHz, etc.). Signals with relatively fast transitions generally require a relatively high bandwidth response. The currents for such fast-transitioning signals may be provided by an external load capacitor (not shown). A possible disadvantage of the regulator 1000 is that it may consume power (e.g., continuously) during its operation.

Figure 14B:
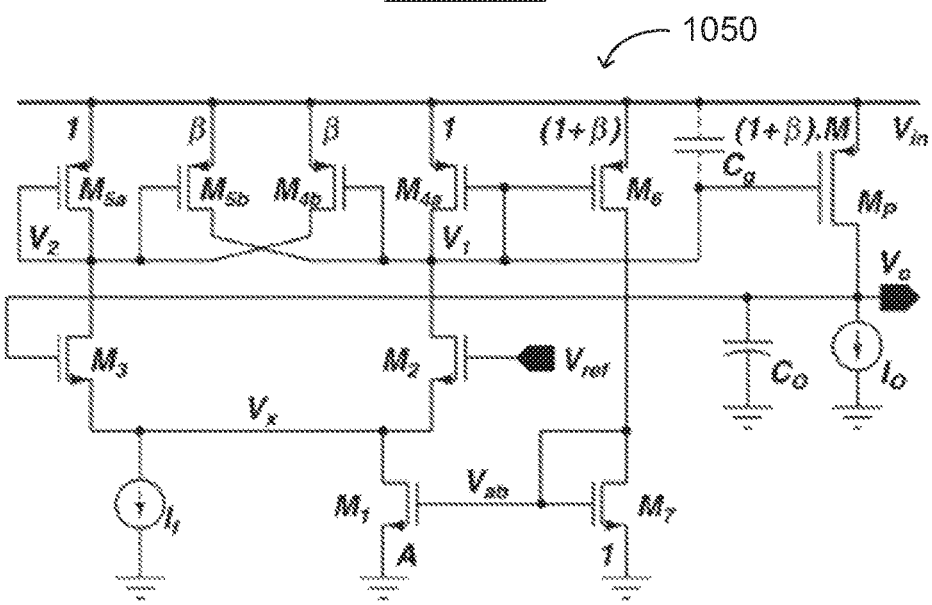

An alternative regulator 1050 (e.g., a single-stage, adaptive biasing or adaptive-biased low-dropout regulator) is shown in FIG. 14B. The adaptive biasing alters the tail current of the error amplifier (transistor $M_p$) in accordance with the load current (e.g., $I_f$). as a result, the regulator 1050 achieves better regulation than fixed-biased, single-stage topologies. One advantage of the regulator 1050 over multiple-stage low-dropout regulators is that the regulation loop (e.g., output $V_o$ controlling the gate of transistor $M_3$) can be easily compensated. The regulator 1050 is configured to regulate an output voltage $V_o$ of 1.0-3.0V, with maximum DC load current of 5-20 μA.

Figure 13B:
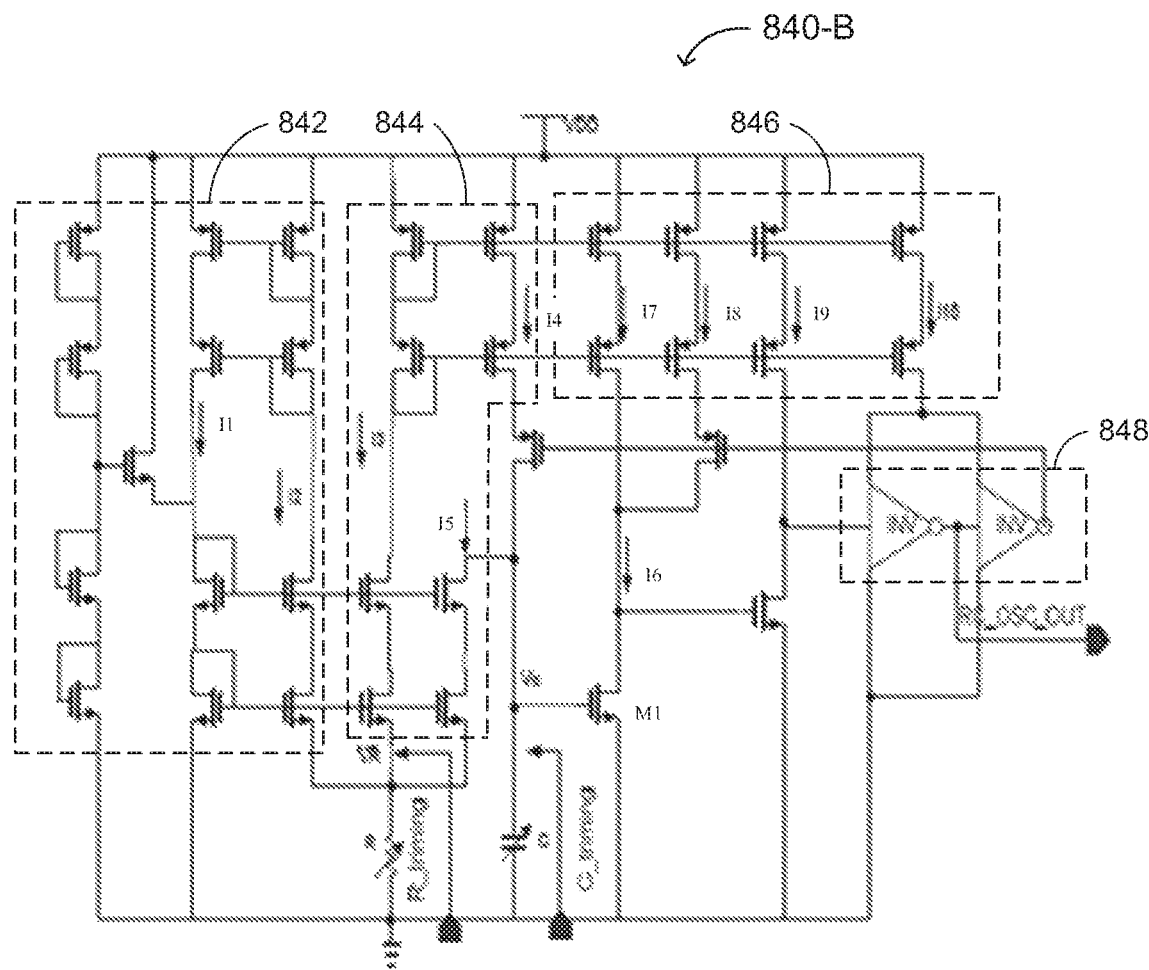

FIG. 13B shows a circuit diagram of an alternative oscillator (e.g., an I-C oscillator) 840-B. The circuit includes a start-up block 842, a current reference block 844, a charge/discharge sensing block 846, and a clock generation block 848. For low-power operating currents, the oscillator 840-B is configured to operate alternately as a current source and as a current sink in the sub-threshold region. The current reference block 844 may be trimmed (e.g., for offsets caused by process variations) using a trimming resistor R_trimming, which controls the power consumption of the oscillator 840-B and which may be internal to the IC 800. A capacitor C_trimming, which may be external to the IC 800 and which may be in parallel with an internal capacitor array, is electrically connected to the sensing node $V_C$ to trim the frequency of the oscillator 840-B. The reference current (I4-I5) charges the node $V_C$. When $V_C$ is above the threshold voltage of transistor M1, the output of the inverters INV shuts off the reference current to the capacitor C_trimming. At this point, the voltage $V_C$ is discharged by the sink current source I5. The frequency of the oscillator 840-B can be calculated according to Equation [2]:

$$\text{Frequency} = \frac{V_R}{2RC\Delta V_C} \quad [2]$$

where R is the resistance of the resistor R_trimming, C is the capacitance of the capacitor C_trimming, and $\Delta V_C$ is the charging/discharging voltage across the capacitor C_trimming.

The frequency of the oscillator 840-B is directly proportional to the resistance R and the capacitance C. It may be important to select and/or manufacture resistor and capacitor components with tight tolerances to meet any requirements for high accuracy of the oscillator 840-B. The frequency of the oscillator 840-B is also dependent on $\Delta V_C$, which may be trimmed on chip and/or off-chip. The frequency of the oscillator 840-B is typically independent of the supply voltage (e.g., to a first order), which may reduce or eliminate the benefit(s) of a low-dropout regulator. The power consumption of the oscillator 840-B is also generally independent of the supply voltage. One disadvantage of the oscillator 840-B may be that the voltage swing on the charging and discharging node $V_C$ is relatively small, which can result in a low signal-to-noise ratio. Also, if an external capacitor is used in the capacitor C_trimming, it may be somewhat prone to ESD.

Figure 13C:
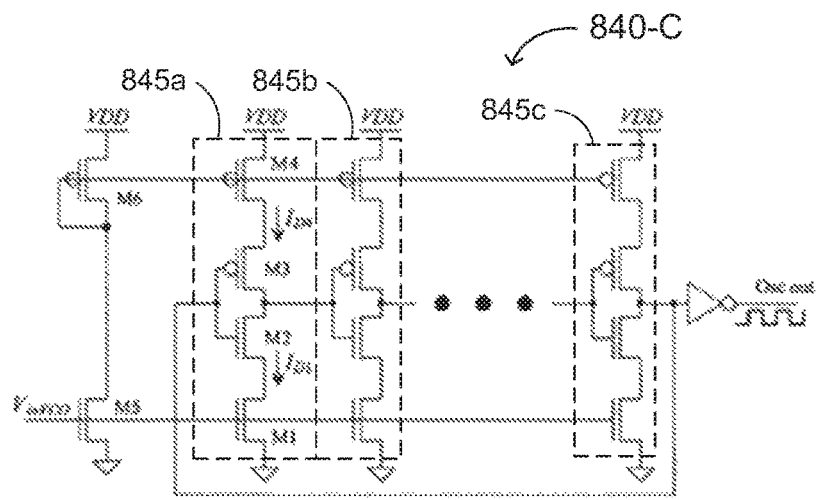

A further alternative low-power oscillator (e.g., a multi-stage current-controlled ring oscillator) 840-C is shown in FIG. 13C. The current-controlled ring oscillator may have any odd number of stages 845*a*-*x* greater than or equal to 3. The bias current $I_{D4}$ to the inverters (e.g., M2 and M3) is controlled by a bias or voltage generator that may be external to the chip 800.

The input voltage $V_{inVCO}$ to the transistor M5 controls the bias current $I_{D4}$ to the inverters. The bias current $I_{D4}$ to the inverters limits the charging and discharging currents, which in turn makes the power consumption of the oscillator 840-C independent of the supply voltage (e.g., VDD). The frequency of the ring oscillator 840-C may be calculated according to Equation [3]:

$$f_{osc} = \frac{I_D}{NV_{DD}C_{TOT}} \quad [3]$$

where N is the number of stages, VDD is the supply voltage, and $C_{TOT}$ is the total capacitance at the output of each inverter. One possible disadvantage of the oscillator 840-C is that the frequency is dependent on the supply voltage VDD, as shown in Equation [3]. The oscillator 840-C may also benefit from a voltage regulator (e.g., to provide VDD and/or $V_{inVCO}$). One advantage of the oscillator 840-C is that its components can be included completely in the IC 800.

Figure 15:
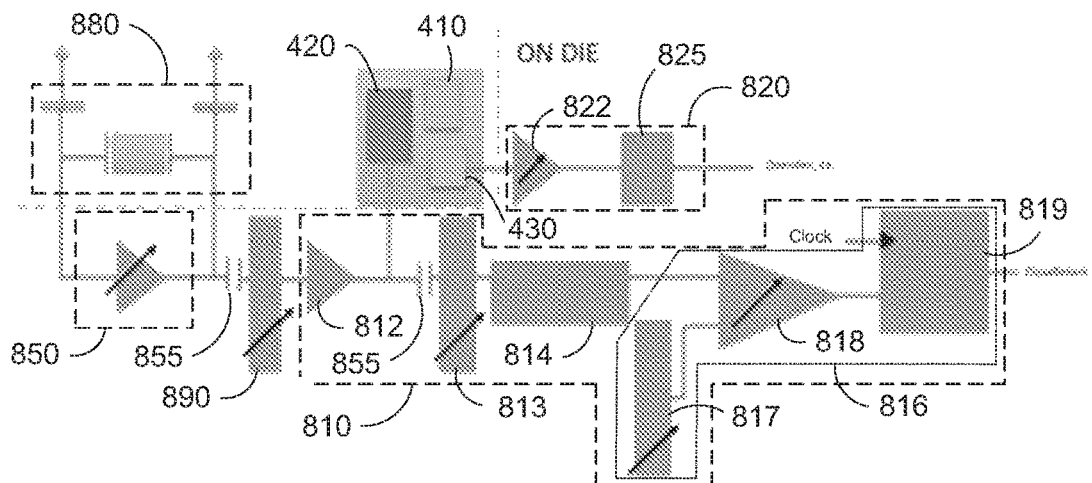
FIG. 15 shows a block diagram of exemplary closed and open state detectors for use with the present continuity sensors, in accordance with one or more embodiments of the present invention.

FIG. 15 shows a block diagram of exemplary components for exemplary closed and open state detectors 810 and 820, similar or identical to those shown in FIG. 12A. The closed and open detectors 810 and 820 may share some circuit elements, although the invention is not limited thereto.

In the path of the closed state detector 810, the output of a crystal oscillator 880 is amplified by an amplifier 850. A tank capacitor 855 receives the amplified crystal oscillator signal, and the output of the tank capacitor 855 is converted to a multi-bit digital signal with a digital-to-analog converter (DAC) 890. The DAC 890 may have a resolution of at least 2 bits (e.g., 3 to 10 bits), but can be relatively simple (e.g., on the order of 5 bits). Thus, the crystal oscillator 880 effectively drives the amplifier 812 for the first stationary coil 420 in the closed state detector 810 with a constant amplitude (e.g., and at a predetermined frequency, such as 13.56 MHz). This process is unaffected by any coupling between the first stationary coil 420 and any other coil.

Thus, the present continuity sensing system may comprise a standard Pierce oscillator. The amplifier 850 may have the highest gain possible that does not saturate the output of the amplifier 812. This may be achieved by adjusting level(s) of the bias to the amplifier 812, which allows the amplifier 812 to successfully detect a closed state (e.g., when the impedance of the tank capacitor 855 changes due to coupling changes in the coils 410, 420 and/or 430). As a result, the amplifier 850 may have a minimum and/or maximum output voltage of 0.8-3.3V (e.g., 1.0 to 2.5 V) at a predetermined frequency (e.g., 13.56 MHz). The gain of the amplifier 850 may be at least 4 times (or, alternatively, at least a minimum increase, such as greater than 8, 10 or 12 dB) when the phase of the periodic signal from the crystal oscillator 880 crosses 0, a measure of positive feedback and oscillatory behavior.

The first stationary coil 420 is a load for the amplifier 812. The distance of the moving coil 410 from the first stationary coil 420 changes the coupling between these coils. A change in coupling between the moving coil 410 and the first stationary coil 420 results in different reflected impedances seen by the amplifier 812. The gain of the amplifier 812 is directly proportional to this impedance. The output voltage swing of the amplifier 812 is a function of the distance or angle between the moving coil 410 and the first stationary coil 420.

The output of the amplifier 812 in the closed state detector 810 is capacitively coupled to a second digital-to-analog converter 813. The digital signal from the second digital-to-analog converter 813 is received by an envelope detector 814 that detects the peak of the digital signal, and the resulting DC voltage is compared against a reference voltage (e.g., from a third DAC 817) in a comparator 818 to generate the final closed/not closed state output. The closed/not closed state output is stored in a latch 819 (e.g., for output as a closed state signal or flag).

The open state detector 820 works on a transmission mode principle, where the strength of the signal transmitted from the first stationary coil 420 to the second stationary coil 430 via the moving coil 410 varies as a function of the distance between the moving coil 410 and the second stationary coil 430. Based on the distance between the moving coil 410 and the second stationary coil 430, the strength of the received signal at the second stationary coil 430 varies. The tank amplifier 822 for the second stationary coil 430 and the circuit blocks downstream therefrom may be configured to provide gain to signals having an amplitude greater than a certain or predetermined threshold.

The threshold for signals to be amplified by the amplifier 822 may be aligned to the distance or angle between the moving coil 410 and the second stationary coil 430. Thus, as the second stationary coil 430 coil and the moving coil 410 couple more strongly, the output signal starts to toggle. The presence of a toggling signal indicates an open state. A static high or low signal indicates a not open state.

The amplifier 812 for the first stationary coil 420 may be important to the performance of both the closed and open detectors 810 and 820. The amplifier 812 may be biased to keep it from saturating, so that information about the closed state and the "not closed" state can be detected. A saturated amplifier output may be unable to distinguish between the two states.

The amplifier 812 may consumes the most power of all of the circuit blocks in FIG. 15, and power management of the amplifier 812 may be beneficial to prolonging the life of the battery. Amplifier gain depends on its bias current. A large and stable gain under varying operating conditions (e.g., load impedances) provides a wide detection window. Detection of closed and open states relies on a changing impedance of the load on the capacitor 855 and/or the capacitor 815 as the coupling between the first stationary coil 420 and the moving coil 410 changes.

The output of the amplifier 812 is converted to a DC value (e.g., by the DAC 813) for input to the envelope detector 814. At particular frequencies (e.g., 13.56 MHz), the output of the amplifier 812 may include some ripple. The envelope detector 814 may comprise a diode and a capacitor. The impedance of the diode and the capacitor in the envelope detector 814 may control the transient performance of the envelope detector 814.

The input to the envelope detector 814 may be trimmed (e.g., by the DAC 813, which may have a resolution of from 3 to 7 bits) and compared to a pre-set reference (e.g., the output of a relatively high-resolution DAC 817, which may have a resolution of from 6 to 12 bits) by a comparator 818. The comparator 818 may comprise a high-gain amplifier that senses the DC voltage output from the envelope detector 814. The comparator 818 uses the reference signal from the DAC 817 to "slice" between closed and not closed states.

The ripple on the DC voltage from the amplifier 812 may reduce the margin available to the comparator 818 for detection of the closed state. This ripple is inversely proportional to the RC value (e.g., of the amplifier 812 and/or circuitry between it and the crystal oscillator 880). To reduce this ripple and improve detection margin, the ripple should be relatively small.

The time during which the closed state and open state detectors 810 and 820 are active (e.g., turned on) may be as small as possible to reduce current consumption and improve battery life. The active mode time of the closed state and open state detectors 810 and 820 may be, for example, from 1 to 50 ms, or any value or range of values therein.

However, if the detector 810 is turned on for a short interval, then the output of the envelope detector 814 may not be fully developed, and the state detection could be erroneous. On the other hand, if the detector 810 is turned on for a longer duration, the detection accuracy is better. Since the envelope detector 810 may consume a relatively large amount of current, the envelope detector 814 turn-on time is a tradeoff between accuracy and battery life. Simulations of the accuracy of the envelope detector 814 as a function of time help to determine an optimal active mode time for the state detector 810 (which is included in the above active mode time range).

The amplifier 822 for the second stationary coil 430 is configured to convert input signals corresponding to an open state into an output signal that can be detected. The output signal is periodic in accordance with the coupling frequency and is ideally a square wave. The amplifier 822 for the second stationary coil 430 amplifies an open state signal, but rejects (does not amplify) a "not open" state signal, from a previous stage (not shown, but which detects the open vs. not open states, and which may comprise a comparator similar to comparator 818 in the closed state detector 810). The amplifier 822 may comprise multiple gain stages. The output waveform (e.g., at 13.56 MHz) from the amplifier 822 may be divided down in frequency by divide-by-n circuit 825 for ease of evaluation and measurement.

A multiplexer 870 (FIG. 12A) may select for output on or through the first stationary antenna 420 (i) an output of the open state detector 820 or the closed state detector 810, or (ii) the wireless (e.g., NFC) communication modulator 860 to a reader (e.g., a smart phone). In absence of the wireless communication field, the open state detector 820 and the closed state detector 810 are typically activated at or after a fixed time interval (e.g., every second, every 15 seconds, every minute, every hour, every day, etc.) to check the continuity state of the package or container. Logic in the IC (e.g., IC 800 of FIG. 12A) can determine the presence of an external wireless frequency source, and shuts off or deactivates the open state/closed state detectors 810/820 upon detecting this frequency of radiation. The multiplexer 870 (which may comprise a plurality of low on-impedance switches) may be configured to switch or enable the first stationary antenna 410 (e.g., FIG. 15) only to communication wirelessly at this time or in this state. The main controller 830 of the IC 800 may activate the second IC 900 and receive a data stream from the second IC 900. The data stream from the second IC 900 (which may comprise a data frame or data packet) is transmitted to the reader by the first IC 800 via the first stationary coil 410 using a conventional wireless communication (e.g., the Tag Talks First, or TTF) protocol. The data may be encoded using a convention encoding scheme (such as On-Off keying and/or Manchester encoding) before transmission.

A block diagram for the second IC 900 is shown in FIG. 12B. The second IC 900 has three power domains. An auxiliary control unit 910 is in the battery power domain, a memory write module 924 (which may comprise a plurality of memory write circuits) and the memory 922 are in a "Battery++" power domain, and the memory read circuits 932 and the wireless communication data processing logic 934 and 936 are in the VDD domain 930.

The second IC 900 may provide any of a number of functions. For example, the second IC 900 may manage and/or process time slot information (as described herein) alone or together with the first IC 800. The second IC 900 may write data to the memory 922 when an event (e.g., a change in the continuity state of the package or container) is detected. The second IC 900 may read different memory elements (e.g., in response to different memory addresses being provided to the auxiliary control 910) and assemble a wireless data frame or packet. In some embodiments, the first IC 800 initiates a memory read operation. The second IC 900 may also read a memory space or address that stores unique ID information, and assembles a correctly sequenced data stream e.g., a data frame) for transmission to the first IC 800. The second IC 900 may dynamically (e.g., in real time) determine error correction code (e.g., the CRC code) when a read operation is initiated. The second IC 900 may also calculate and/or update the CRC as product usage data (e.g., a cumulative number of open and closed states) is recorded in the memory 922. The second IC 900 may output a data package for wireless communication in a serial format to the first IC 800 for encoding and/or modulation, or may perform either or both of the encoding and modulation functions itself. The second IC 900 may synchronize its operations with those of the controller 830 in the first IC 800 to keep the overall system synchronized.

In some embodiments, a memory read operation is initiated (e.g., by the main controller 830) when a reader is in the vicinity (e.g., within 3-10 meters, 3-10 cm, etc.) of the first stationary coil 410 (e.g., FIGS. 5, 8, and 15). The memory read operation can be initiated even if the battery is depleted or discharged. When the reader energizes the first IC 800 (e.g., by power extraction using the first stationary coil 410 and a rectifier coupled thereto), the main controller 830 may generate and transmit to the second IC 900 (*i*) a supply voltage sufficiently high for at least the memory 922, the memory read circuits 932, and the data processing circuits 934 and 936 to perform the memory read functions and (ii) a periodic (e.g., clock) signal for the memory read functions. Once the supply voltage and periodic signal are received by the second IC 900, the second IC 900 initiates a memory read operation (e.g., according to a standard wireless communication protocol). The data package (or payload) may be divided between identification information (which may be hardcoded in the second IC 900 using laser-blown fuses), information in the memory 932 (which may include open state and closed state information), and error code (which may be calculated using a standard algorithm). The error code may be generated every time a read operation is performed because the information stored in the memory 922 may have changed since the most recent read operation. In some embodiments, the entire memory 922 is read and serially transported to the first IC 800, where the data are encoded and modulated for transmission to the reader.

The main controller 830 is in the first IC 800. The control bus (not shown; e.g., between the first and second ICs 800 and 900, or in the continuity state sensing system) encodes the state of the main controller 830 in the first IC 800, the state of any error flags, and the state of the auxiliary controller 910 in the second IC 900. The first IC 800 and the second IC 900 are synchronized using this bus so that each IC is in the correct state during operation.

On system start-up, the second IC 900 initializes a memory address counter (e.g., in the read circuits 932) to a start bit (e.g., a first addressed bit in the memory 922), writes to a start flag location, and moves the memory address counter to the next location (address) in the memory 922. Every time an open state is detected, a corresponding bit in the memory 922 is written, and the address counter (e.g., an "open state" address counter) is incremented. The "open state" address counter may also be incremented at the end of a predetermined time period (e.g., every hour, every 8 hours, every day, etc.). without writing to a corresponding memory bit. The portion of the memory and an address counter corresponding to closed state detection can operate similarly or identically. This allows the system to keep a record of open state and closed state detections (and, optionally, the time and/or time periods in which such detections were made). in some embodiments, the present continuity state sensing system may record a maximum number of open and/or closed states, or a maximum length of time of operation, in which case it sets an "end-of-life" flag and writes to the memory location corresponding to the flag.

The memory write circuits 924 may use the battery voltage to pump up the voltage to a "Battery++" level. In other words, if the battery voltage is ×V, then the "Battery++" voltage is >×V (e.g., ≥1.2×, ≥1.3×, ≥1.5×, etc.). When the memory comprises nonvolatile cells (e.g., one-time programmable cells, EPROM cells, etc.), a voltage greater than the battery voltage may be needed to write to the cell.

In some embodiments, the memory 922 comprises a non-volatile memory array that, along with programming circuits in the write module 924, allows storage of information at a level or resolution of a single bit. The memory 922 may be used to store time stamps of open/closed state detection events, as well as the data itself. In one embodiment, the memory 922 stores usage data (e.g., the number of sequential open state-closed state detection events), along with error flags (e.g., a "partially open" or "partially closed" state, preceded and followed by the same continuity state) and other information that can be analyzed (e.g., by software) to determine compliance with product usage instructions.

Figure 16:
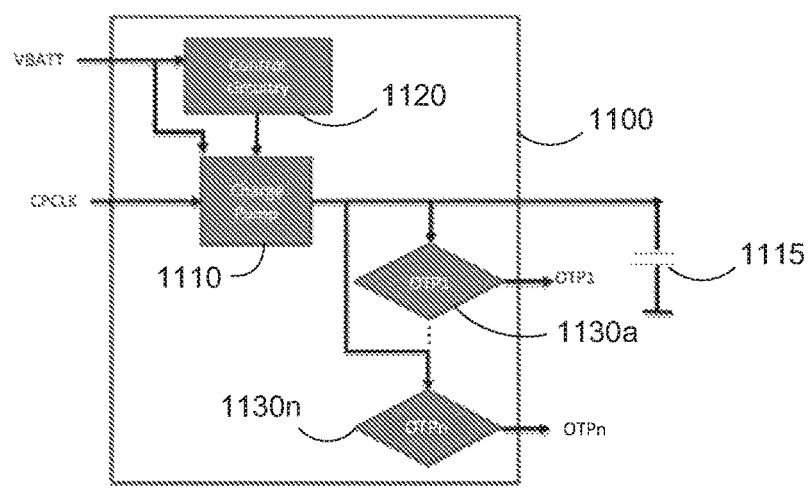
FIG. 16 shows control circuits for programming and/or writing to a nonvolatile memory in accordance with one or more embodiments of the present invention.

For the write operation to nonvolatile memory to occur successfully, a voltage higher than the battery voltage is generated using a charge pump (e.g., charge pump 1110 in the exemplary nonvolatile memory programming circuitry 1100 in FIG. 16). The charge pump 1110 may include switches controlled by a clock signal (e.g., CPCLK) to transfer charge (e.g., VBATT) from the battery (not shown) to a storage capacitor 1115 that develops the write voltage across its terminals. Upon receiving a write request (e.g., in the main controller 830), a voltage is applied to program a nonvolatile memory (e.g., OTP) cells 1130*a-n*. In some embodiments, programming comprises applying a voltage sufficiently high to break down a dielectric layer in the memory cell. Meanwhile, the storage capacitor rebuilds charge and is ready to transfer it into the next memory cell when a write request for that cell is provided (e.g., to the main controller 830).

The control circuits for programming and/or writing to the nonvolatile memory 1130*a-n* are shown in FIG. 16. These circuits include the charge pump 1110, the storage capacitor 1115, and a control circuit 1120. The nonvolatile memory 1130*a-n* includes n individual nonvolatile memory cells, where n is an integer of at least 4 (e.g., 2×, where x is an integer of at least 3), and each cell stores one bit of data. The nonvolatile memory 1130*a-n* may be a single row or column of cells, or an array of 2 or more rows and 2 or more columns. The individual nonvolatile memory cells may be accessed by corresponding address signals.

In some embodiments, the frequency of the clock signal (e.g., CPCLK) may be varied with differing values of the storage capacitor. As a result, the voltage to program or write into a nonvolatile memory cell 1130*a-n* may be programmable as well. The circuitry associated with programming the nonvolatile memory cells 1130*a-n* may be active or turned on only for the duration of a read or write/program operation, during which time an enable signal may be provided to the circuit block 1100. Power consumption from the battery may therefore be limited to the time interval when the enable signal is active.

Figure 17:
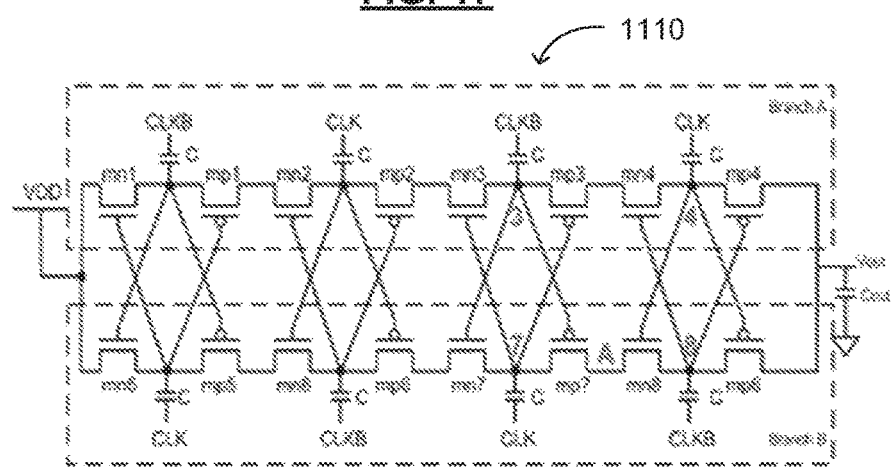
FIG. 17 shows an exemplary charge pump suitable for programming the nonvolatile memory of FIG. 16 in accordance with one or more embodiments of the present invention.

An exemplary charge pump 1110 is shown in detail in FIG. 17. The charge pump 1110 is configured to increase the voltage from the battery to a level sufficient to enable the write operation (e.g., program the nonvolatile memory cells 1130*a-n* in FIG. 16). The charge pump 1110 uses switches mn1-8 and mp1-8, controlled by a clock signal (e.g., CLK and its complement, CLKB) to transfer charge from the battery (VBATT in FIG. 16, VDD in FIG. 17) to a storage capacitor Cout. Upon receiving an instruction to program one or more nonvolatile memory cells 1130*a-n*, the charge stored on the capacitor Cout is transferred to the nonvolatile memory cell(s), and the voltage necessary to program the cell(s) (e.g., by breaking down a thin dielectric layer in the cell) is applied to the cell(s). The charge pump 1110 is configured to deliver a minimum programming voltage (e.g., at least 3V, 4V, 5V, etc., but >the battery voltage or VDD) and/or a maximum or excess current (e.g., up to 2 mA, 4 mA, 6 mA, etc.) for a short duration of time (e.g., 1-1000 ms, or any value or range of values therein). Upon delivery of the programming voltage, the impedance of the programmed memory cell 1130 is significantly reduced. Measurement of the impedance may validate a successful programming operation. The PIC 900 (FIG. 12B) also contains control circuitry (not shown) configured to regulate the charge pump voltage at a desired or predetermined voltage for the duration of the write operation.

Alternatively, a Dickson charge pump (not shown) may be used instead of the charge pump 1110 in FIG. 17. The Dickson charge pump comprises a plurality of MOS switches (e.g., NMOS transistors connected in series between source/drain terminal of adjacent switches, the first of which is connected as a diode such that the input voltage is received at both a source/drain terminal and the gate), controlled by different phases of a clock signal (e.g., that are 180° apart). The clock signal may be provided by a clock generator that is external to the second IC 900. The charge is transferred from one switch to the next and stored in intermediate "flying" capacitors (e.g., having one electrode receiving one phase of the clock signal and another electrode connected to the gate of a MOS switch), and finally into a storage capacitor that provides the programming voltage. The programming voltage in the Dickson charge pump depends on number of stages in the pump, the flying capacitors (e.g., the capacitances thereof), and the frequency of the clock.

In order to mitigate the potential impact of a breakdown voltage on the MOS switches in the Dickson charge pump, a modified Dickson charge pump may be used as shown in FIG. 17. The gate-source and gate-drain voltages at the switches mn1-8 and mp1-8 are kept below the battery voltage VDD, even though the absolute voltage developed across each stage may increase by a factor of up to 2. However, the modified charge pump architecture shown in FIG. 17 may increase the number of capacitors C (each stage may include two capacitors C), thereby increasing the real estate consumed by the charge pump 1115.

The charge pump 1110 may also include a buffer (not shown) driving the gates of the MOS switches mn1-8 and mp1-8. In some embodiments, the buffer may comprise a plurality of inverter stages connected in series (i.e., the output of a first inverter is an input to a second inverter) and a logic gate (e.g., a NAND or AND gate) at an input of the plurality of inverter stages (e.g., receiving at least the clock signal CLK and an enable signal), where the plurality of inverter stages are configured to output the clock signal CLK and its complement CLKB. The buffers may be sized so that they can operate at high frequency (e.g., >500 kHz, 900 kHz, >13 MHz, etc.) and drive the gates of the MOS switches mn1-8 and mp1-8 close to the supply voltage VDD and ground to effectively transfer the charge across the switches. Any leakage in the capacitors C due to equivalent series resistance (ESR) may affect the output voltage Vout, and should be minimized to the extent possible under the circumstances.

Cyclic Redundancy Checking (CRC) is a technique for detecting (and optionally correcting) errors in digital data that may be transmitted as a long string of serial digital data bits. For example, the CRC code added by the dynamic CRC circuit 934 (FIG. 12B) to the data from the read circuits 932 may comprise p bits (e.g., where p is an integer of at least 2, such as 4, 8, 10, 16, etc.), attached to a serial payload of q bits (e.g., where q is an integer of at least 60, 120, 180, 240, etc.). The sum of p+q may conform to a known protocol for wireless transmission of serial data (e.g., where [p+q]=64, 128, 192, 256, etc.). The dynamic CRC circuit 934 attaches the CRC code to the data string using a standard polynomial. The receiver (e.g., a smart phone; not shown) validates an error-free transmission by applying the same polynomial to the received data and comparing the result to the received CRC code. In case of a discrepancy (a logic 0 or a logic 1 was received in error), the comparison (e.g., a CRC check) will fail, and the receiver will discard the incorrect data.

Figure 18:
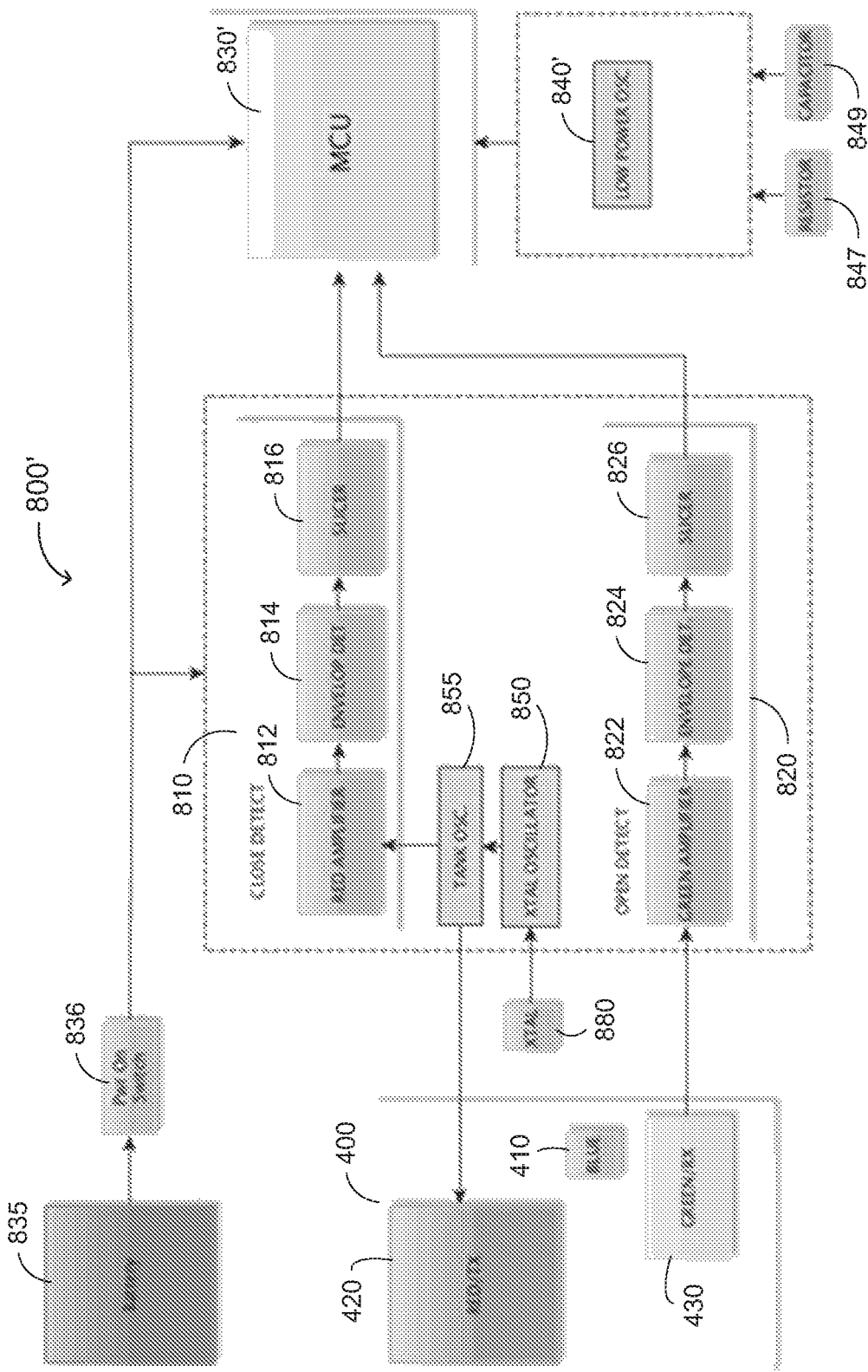
FIG. 18 shows an exemplary system including the present continuity sensor in accordance with one or more embodiments of the present invention.

In a further embodiment, the continuity sensor may comprise the system 800' shown in FIG. 18. The system 800' comprises an external MCU 830' that functions as the main controller (e.g., 830 in FIG. 12A), the present open state-closed state sensor 400/810/820, a battery 835 and power management functionality. The power management functionality comprises a conventional power-on switch 836 that reduces or minimizes battery drain while the sensor is not in use. In a further embodiment, the power-on switch 836 can also electrically disconnect (e.g., turn off) the battery supply to the circuitry in the system 800'. At least one of the circuits (e.g., the MCU 830') is configured to transmit signals in accordance with a wireless protocol (e.g., to read and/or report the time at which the package or container is opened). The MCU 830' and the IC comprising the present open state and closed state detectors 810 and 820 are in different clock domains during operation. In at least one embodiment, the low power oscillator 840' that provides one or more timing signals to the MCU 830' may comprise an external resistor 847 and an external capacitor 849. The components having an identification number identical to a component in another Figure operate identically or substantially identically to the component in the other Figure (as described herein).

Figure 19:
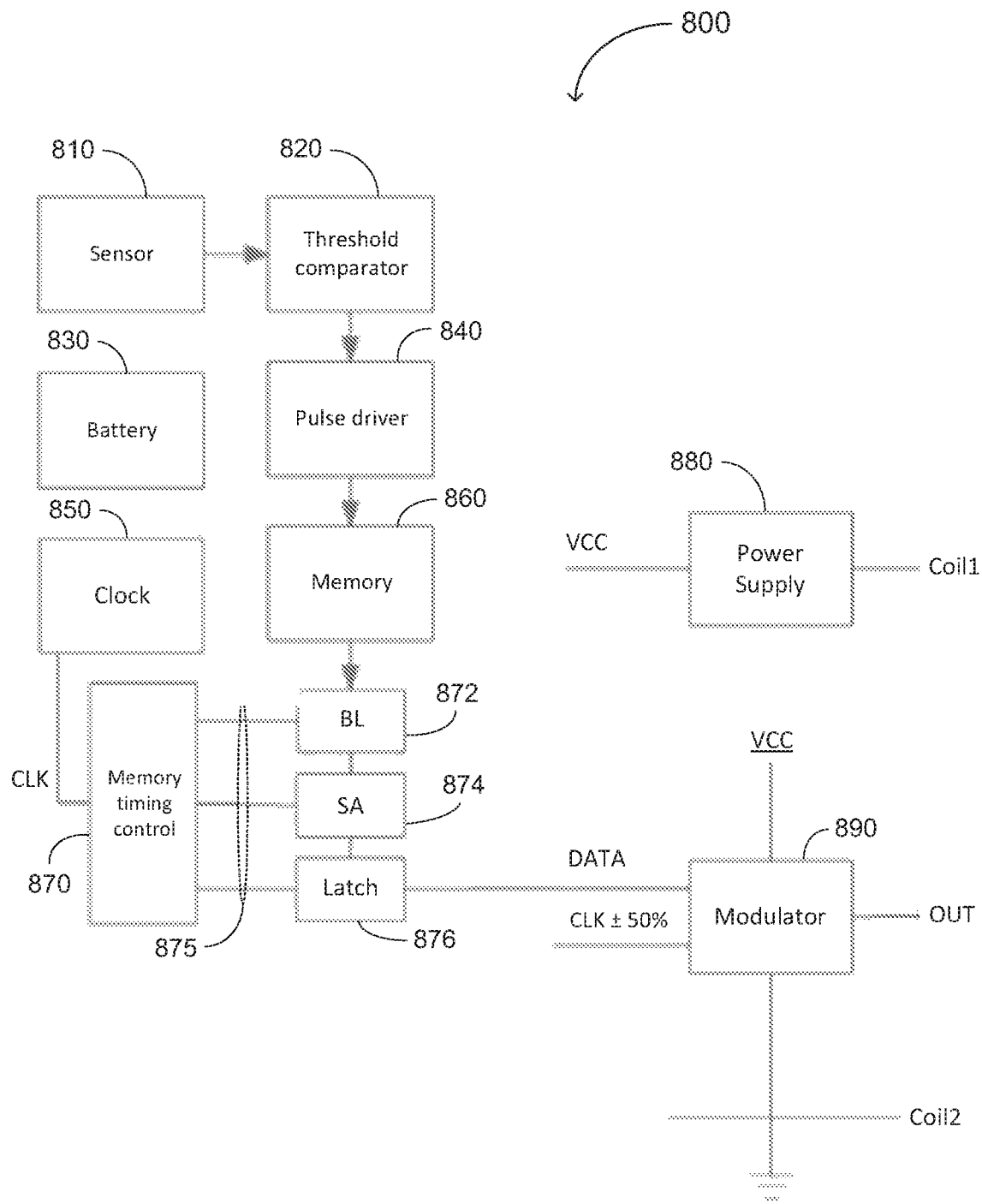
FIG. 19 shows a diagram of another exemplary integrated circuit suitable for use with the present continuity sensors, in accordance with one or more embodiments of the present invention.

FIG. 19 shows another exemplary integrated circuit 1200 for use in the present device. Some or all of the circuit and/or functional blocks in the exemplary integrated circuit 1200 can be present in the integrated circuit in any embodiment of the present invention. Additional circuit blocks, such as one or more display drivers, can also be included in certain embodiments.

The exemplary integrated circuit (IC) 1200 for use with the present security device includes one or more sensors (e.g., the present continuity sensor) 1210, a threshold comparator 1220 receiving information (e.g., a signal) from the sensor(s) 1210, a pulse driver 1240 receiving an output of the threshold comparator 1220, a memory 1260 storing sensor data from the pulse driver 1240, one or more bit lines (BL) 1272 for reading data from the memory 1260, one or more sense amplifiers (SA) 1274 for converting the signal(s) on the bit line(s) to digital signals, one or more latches 1276 for temporarily storing data from the sense amplifier(s), and a transmitter (e.g., modulator) 1290 configured to output data (including an identification code) from the device. The exemplary IC 1200 in FIG. 12 also contains a clock (e.g., oscillator) 1250 configured to provide a timing signal (e.g., CLK) that controls the timing of certain operations in the IC 1200 and a memory timing control block or circuit 1270 that controls the timing of memory read operations. The modulator 1290 also receives the timing signal (CLK) from the clock circuit or a slowed-down or sped-up variation thereof. The exemplary IC 1200 may also include a power supply block or circuit 1280 that provides a direct current (e.g., VCC) to various circuits and/or circuit blocks in the IC. The memory 1260 may also contain identification code. The portion of the memory 1260 containing identification code may be printed. The IC 1200 may further contain a receiver (e.g., a demodulator), one or more rectifiers (e.g., a rectifying diode, one or more half-bridge or full-bridge rectifiers, etc.), one or more tuning or storage capacitors, etc. Terminals in the modulator 1290 and the power supply 1280 may be connected to ends of an antenna (e.g., at Coil1 and Coil2). The antenna may be a stationary (e.g., the second or third) coil, as described herein. In one embodiment, the IC 1200 further comprises one or more display drivers, and the battery 1230 and/or the power supply 1280 may be connected to one or more leads providing power to the display driver(s) and optionally a ground plane or other ground potential.

The memory in a wireless (e.g., an NFC or RF) security device may contain a fixed number of bits. In some implementations, an NFC tag may contain 128 or 256 bits. Some bits are allocated to overhead (non-payload) data for format identification and data integrity (CRC) checking. The payload of the wireless device consumes the remainder of the bits. For example, the payload can be up to 96 bits in the case of the 128-bit NFC tag and up to 224 bits in the case of the 256-bit NFC tag.

The payload of the NFC device can be allocated to variable amounts of fixed ROM bits (which are generally—but not always—used as a unique identification number). When print methods are used in manufacturing the NFC device, the ROM bits are permanently encoded and cannot be electrically modified. Any payload bits that are not allocated as fixed ROM bits can be allocated as dynamic sensor bits (e.g., for the continuity sensor). These sensor bits can change values, based on a sensed input. Different splits or allocations between ROM and sensor bits are indicated by data format bits that are part of the non-payload or 'overhead' bits, generally in the first 16 bits of the NFC tag memory.

One example of how continuity sensing may be implemented in the present invention involves a sensor 1210 that detects the voltage on a stationary coil, as described herein. The detected voltage is compared to a threshold voltage in the threshold comparator 1220, which outputs a digital or analog value corresponding to a continuity state of the package or container, and the pulse driver 1240 stores the value in the memory 1260. In a relatively simple example, when the voltage detected on the first stationary coil is equal to or greater than the threshold voltage of the "closed state" sensor, the package or container is closed, and when the voltage detected on the second stationary coil is equal to or greater than the threshold voltage of the "open state" sensor, the package or container is open. When the voltages detected on both stationary coils are less than the corresponding threshold voltages, the package or container is partially closed or partially open. Thus, one or more continuity state bits in the memory 1260 store a state that reflects the detected voltage(s). This indicates to the reader (e.g., an NFC smartphone, etc.) that the protected container is closed, open, or somewhere in-between. The ROM ID bits do not change, but any data integrity bits (e.g., for CRC) may be updated to reflect the continuity state of the package or container.

The IC 1200 in the present device may include one or more other sensors in addition to the continuity sensor(s). For example, the IC 1200 can further include one or more temperature sensors, humidity sensors, electromagnetic field sensors, current/voltage/power sensors, light sensors, and/or chemical sensors (e.g., for oxygen, carbon monoxide, carbon dioxide, nitrogen oxides, sulfur dioxide and/or trioxide, ozone, one or more toxins, etc.). The present IC may also include one or more time sensors (e.g., configured to count or determine elapsed time), which may include the clock circuit (which can be a basis for a real-time clock) 1250 and one or more counters, dividers, etc., as is known in the art. Such sensors may be on the same substrate as the antenna (e.g., one of the stationary coils), the battery 1250 and/or the IC 1200, or on a different substrate that is electrically connectable to the battery 1250 and the IC 1200.

Each of the embodiments of the invention described with reference to the Figures may be modified by the disclosures connected to the other embodiments and/or by the other disclosures herein, including in the 'Summary of the Invention' section and the claims.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

The invention claimed is:

1. A multi-state article which comprises a sensor for sensing when the article is in at least a first one of its states, the sensor comprising a system of coils which is adapted to provide a coil coupling which is representative of the first state when the article is in the first state;
   wherein the article comprises a first structure, which is provided with at least one coil of the coil system of the sensor, and a second structure, which is provided with the rest of the coils of the coil system of the sensor, and the first and second structures are movable relative to one another to move the article between its first state and a second state and to change the position of the least one coil relative to the rest of the coils to change the coupling in the coil system thereby to sense when the article is in its first state, and;
   wherein the at least one coil comprise a bridging coil and the rest of the coils comprise a driver coil and a detector coil and wherein in the first state of the article the driver coil is able to couple with the detector coil through the bridging coil to provide a coupling with the detector coil which is representative of the first state.

2. The article of claim 1, wherein the article comprises a prescribed usage regime and wherein the sensor comprises an adherence sensor for sensing article use events and storing a use event history, the sensor comprising a NFC antenna for wireless transfer of the use history.

3. The article of claim 2, wherein the NFC antenna enables wireless communication between the sensor and another NFC-enabled article of sensor data concerning the use event history.

4. The article of claim 1, wherein the sensor is an electronic sensor of which at least the coil system is printed.

5. The article of claim 1, wherein in the second state the bridging coil couples with the driver coil to provide a coupling which is representative of the second state of the article.

6. The article of claim 1, wherein the driver coil is a NFC antenna.

7. The article of claim 1, wherein the sensor is an electronic device which comprises a memory to store sensor data representative of the states sensed.

8. The article of claim 7, wherein the sensor is adapted to store in memory time data associated with the state data.

9. The article of claim 1, wherein the article has open and closed states as its first and second states.

10. The article of claim 1, wherein the article is manually operable to effect its change of state.

11. The article of claim 1, which is a multi-use, multi-state article.

12. The article of claim 11, wherein the article contains or is adapted to contain a supply of substance which is to be dispensed or made available for dispensing over the course of a number of uses until the supply is empty or is deemed empty.

13. The article of claim 1, wherein the article is an inhaler.

14. The article of claim 1, wherein the sensor includes a signal generator adapted to produce a signal when the article is in said first state which is representative of the article being in the first state, and wherein the signal generator is a coil in the system of coils, wherein the coil comprises an NFC antenna.

15. A multi-state article which comprises a sensor for sensing when the article is in at least a first one of its states, the sensor comprising a system of coils which is adapted to provide a coil coupling which is representative of the first state when the article is in the first state;
wherein the article contains or is adapted to contain a supply of substance which is to be dispensed or made available for dispensing over the course of a number of uses until the supply is empty or is deemed empty; and
wherein the article is an inhaler.

16. The article of claim 15, which is further adapted to provide a coil coupling which is representative of a second state, different from the first state, of the article when the article is in the second state.

17. The article of claim 15, wherein the coils are adapted to adopt different coil configurations including a first coil configuration which is adopted when the article is in the first state and which is able to provide the coil coupling which is representative of the first state.

18. The article of claim 17, wherein the coil system further has a second coil configuration which is adopted when the article is in a second state, different from the first state, of the article and which is able to provide a coil coupling which is representative of the second state.

19. The article of claim 18, wherein movement of the article between its first and second states causes the coil system configuration to move to the coil configuration which corresponds to the respective article state.

20. The article of claim 15, wherein the sensor comprises a near-field communication (NFC) antenna.

21. The article of claim 20, wherein the sensor includes a signal generator adapted to produce a signal when the article is in said first state which is representative of the article being in the first state, and wherein the signal generator is a coil in the system of coils, wherein the coil comprises the NFC antenna.

22. The article of claim 15, wherein the sensor includes a movable first coil which moves with respect to at least one other coil as the article moves between its different states.

23. The article of claim 22, wherein the movable first coil is movable between first and second positions, the first of which is the position of the movable first coil in the first state of the article.

24. The article of claim 23, wherein the sensor has second and third coils and in the first position the movable first coil is disposed adjacent to the second coil for a coupling therewith representative of the article being in the first state.

25. The article of claim 24, wherein in its second position the movable first coil is disposed adjacent the third coil for a second coupling therewith which is representative of the article being in a second state.

26. The article of claim 15, wherein the article comprises a first structure, which is provided with at least one coil of the coil system of the sensor, and a second structure, which is provided with the rest of the coils of the coil system of the sensor, and the first and second structures are movable relative to one another to move the article between its first state and a second state and to change the position of the least one coil relative to the rest of the coils to change the coupling in the coil system thereby to sense when the article is in its first state and, optionally, its second state.

27. The article of claim 15, wherein the inhaler is a multi-dose dry powder inhaler.

28. The article of claim 15, wherein the article has an open-use-close operating sequence.

29. The article of 28, wherein the article has an outlet and a closure therefor and the article is moved between closed and open states by moving the closure from a closed position, in which it closes the outlet, to an open position, in which the outlet is opened.

30. The article of claim 29, wherein the closure is a mouthpiece cover and actuator of the inhaler.

31. The article of claim 15, wherein the article comprises a prescribed usage regime and wherein the sensor comprises an adherence sensor for sensing article use events and storing a use event history, the sensor comprising a NFC antenna for wireless transfer of the use history.

32. The article of claim 31, wherein the NFC antenna enables wireless communication between the sensor and another NFC-enabled article of sensor data concerning the use event history.

33. The article of claim 15, wherein the sensor is an electronic sensor of which at least the coil system is printed.

34. The article of claim 15, wherein the sensor is an electronic device which comprises a memory to store sensor data representative of the states sensed.

35. The article of claim 34, wherein the sensor is adapted to store in memory time data associated with the state data.

36. The article of claim 15, wherein the article has a second state, and said article is open and capable of dispensing substance in its first state and closed and incapable for dispensing substance in its second state.

37. The article of claim 15, wherein the article is manually operable to effect its change of state.

* * * * *